US012714424B1

(12) United States Patent
Prosser et al.

(10) Patent No.: US 12,714,424 B1
(45) Date of Patent: Aug. 25, 2026

(54) TECHNOLOGIES FOR HOMING A MOTOR OF A SURGICAL STAPLER

(71) Applicant: Cilag GmbH International, Zug (CH)

(72) Inventors: Christopher N. Prosser, Cincinnati, OH (US); Christopher Moell, Cincinnati, OH (US); Jared Speichinger, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/311,637

(22) Filed: Aug. 27, 2025

(51) Int. Cl.

| | |
|---|---|
| ***A61B 17/064*** | (2006.01) |
| ***A61B 17/072*** | (2006.01) |
| ***A61B 90/00*** | (2016.01) |
| *A61B 17/00* | (2006.01) |

(52) U.S. Cl.
CPC ........... *A61B 17/072* (2013.01); *A61B 90/03* (2016.02); *A61B 2017/00039* (2013.01); *A61B 2017/00075* (2013.01); *A61B 2017/00212* (2013.01); *A61B 2017/00398* (2013.01); *A61B 2017/00725* (2013.01); *A61B 2017/07285* (2013.01); *A61B 2090/066* (2016.02)

(58) Field of Classification Search
CPC . A61B 17/072; A61B 90/03; A61B 2090/066; A61B 2017/00039; A61B 2017/00075; A61B 2017/00212; A61B 2017/00398; A61B 2017/00725; A61B 2017/07285
See application file for complete search history.

(56) References Cited

U.S. PATENT DOCUMENTS

| | | | |
|---|---|---|---|
| 5,395,033 | A | 3/1995 | Byrne et al. |
| 7,644,848 | B2 | 1/2010 | Swayze et al. |
| 7,721,931 | B2 | 5/2010 | Shelton, IV et al. |
| 8,753,338 | B2 | 6/2014 | Widenhouse et al. |
| 9,265,585 | B2 | 2/2016 | Wingardner et al. |
| 9,615,888 | B2 | 4/2017 | Manzo et al. |
| 9,668,735 | B2 | 6/2017 | Beetel |
| 9,877,718 | B2 | 1/2018 | Weir et al. |
| 10,190,888 | B2 | 1/2019 | Hryb et al. |
| 10,206,678 | B2 | 2/2019 | Shelton, IV et al. |
| 10,271,844 | B2 | 4/2019 | Valentine et al. |
| 10,595,836 | B2 | 3/2020 | Smaby et al. |

(Continued)

FOREIGN PATENT DOCUMENTS

| | | | |
|---|---|---|---|
| EP | 0679367 | A2 | 11/1995 |
| EP | 2364666 | A1 | 9/2011 |

(Continued)

*Primary Examiner* — Eyamindae C Jallow
(74) *Attorney, Agent, or Firm* — Barnes & Thornburg LLP

(57) ABSTRACT

Technologies for homing a motor of a surgical stapler system includes a control system configured to determine a targe drive voltage for the motor that is configured to set a speed of the motor to zero at a reference torque threshold. The reference torque threshold is indicative of contact between a rotation limiter operatively coupled to the motor and a rotation hardstop. The control system further controls the motor to rotate in a first direction until the motor stalls, which is indicative of contact between rotation limiter and the rotation hardstop. The control system further determines a present position of the motor in response to the stalling of the motor and sets the present position of the motor as a maximum motor position for the first direction.

20 Claims, 15 Drawing Sheets

(56) References Cited

U.S. PATENT DOCUMENTS

| | | | |
|---|---|---|---|
| 10,828,030 | B2 | 11/2020 | Weir et al. |
| 11,559,366 | B2 | 1/2023 | Overmyer et al. |
| 11,653,915 | B2 | 5/2023 | Shelton, IV et al. |
| 11,931,037 | B1 * | 3/2024 | Shelton, IV ..... A61B 17/07207 |
| 11,937,816 | B2 | 3/2024 | Huang |
| 11,992,210 | B2 | 5/2024 | Shelton, IV et al. |
| 12,082,806 | B2 | 9/2024 | Giordano et al. |
| 12,268,388 | B2 | 4/2025 | Fiebig et al. |
| 12,484,900 | B2 | 12/2025 | Ryle et al. |
| 12,544,067 | B2 | 2/2026 | Batty et al. |
| 2014/0005654 | A1 * | 1/2014 | Batross .......... A61B 17/320092 606/171 |
| 2014/0114334 | A1 * | 4/2014 | Olson ............ A61B 17/320092 606/169 |
| 2016/0030042 | A1 | 2/2016 | Heinrich et al. |
| 2018/0042658 | A1 | 2/2018 | Shelton, IV et al. |
| 2019/0015102 | A1 | 1/2019 | Baber et al. |
| 2019/0099180 | A1 * | 4/2019 | Leimbach .............. G16H 20/40 |
| 2019/0200997 | A1 | 7/2019 | Shelton, IV et al. |
| 2019/0200998 | A1 * | 7/2019 | Shelton, IV ....... A61B 17/1155 |
| 2019/0201046 | A1 * | 7/2019 | Shelton, IV ........... G16H 50/20 |
| 2019/0201047 | A1 * | 7/2019 | Yates ..................... H04N 7/183 |
| 2021/0045827 | A1 * | 2/2021 | Asadian ................. A61B 90/03 |
| 2024/0366221 | A1 | 11/2024 | Marriott et al. |
| 2024/0415510 | A1 | 12/2024 | Schings et al. |
| 2024/0423615 | A1 | 12/2024 | Shelton, IV et al. |
| 2025/0000510 | A1 | 1/2025 | Creamer et al. |
| 2025/0017585 | A1 | 1/2025 | Nalagatla et al. |
| 2025/0025155 | A1 | 1/2025 | Batty et al. |
| 2025/0025156 | A1 | 1/2025 | Shelton, IV et al. |
| 2025/0025157 | A1 | 1/2025 | Batty et al. |
| 2025/0025158 | A1 | 1/2025 | Ryle et al. |
| 2025/0025159 | A1 | 1/2025 | Batty et al. |
| 2025/0025160 | A1 | 1/2025 | Batty et al. |
| 2025/0025162 | A1 | 1/2025 | Ahrens et al. |
| 2025/0025164 | A1 | 1/2025 | Batty et al. |
| 2025/0025165 | A1 | 1/2025 | Ryle et al. |
| 2025/0025167 | A1 | 1/2025 | Ryle et al. |
| 2025/0025168 | A1 | 1/2025 | Ryle et al. |
| 2025/0025169 | A1 | 1/2025 | Batty et al. |
| 2025/0025170 | A1 | 1/2025 | Bertram et al. |
| 2025/0120697 | A1 * | 4/2025 | Shelton, IV ......... A61B 17/072 |
| 2025/0120718 | A1 | 4/2025 | Shelton, IV et al. |
| 2025/0312040 | A1 | 10/2025 | Overmyer |
| 2025/0375200 | A1 | 12/2025 | Batty et al. |

FOREIGN PATENT DOCUMENTS

| | | | | |
|---|---|---|---|---|
| EP | 2923661 | A2 * | 9/2015 | ............. A61B 90/98 |
| WO | 2012112249 | A1 | 8/2012 | |

* cited by examiner

1600

B

1602 PERFORM STAPLER INITIALIZATION?

NO

YES

1604 DETERMINE TARGET DRIVE VOLTAGE FOR MOTOR REQUIRED TO SET MOTOR SPEED TO ZERO AT REFERENCE TORQUE THRESHOLD

1606 RETRIEVE TARGET DRIVE VOLTAGE VALUE FROM DATA STORAGE

1608 DETERMINE TARGET DRIVE VOLTAGE BASED ON MOTOR PARAMETERS

1610 PERFORM CALIBRATION PROCEDURES TO ESTIMATE MOTOR PARAMETERS

1612 CONTROL MOTOR TO MOVE IN FIRST DIRECTION USING TARGET DRIVE VOLTAGE UNTIL MOTOR STALL

1614 DETECT MOTOR STALL BASED ON MOTOR MOVEMENT

1616 SET PRESENT MOTOR POSITION AS MAXIMUM POSITION FOR FIRST DIRECTION

1618 CONTROL MOTOR TO MOVE IN SECOND DIRECTION USING TARGET DRIVE VOLTAGE UNTIL MOTOR STALL

1620 SET PRESENT MOTOR POSITION AS MAXIMUM POSITION FOR SECOND DIRECTION

1622 CONTROL OPERATION OF SURGICAL STAPLER USING DETERMINED MAXIMUM POSITIONS FOR MOTOR

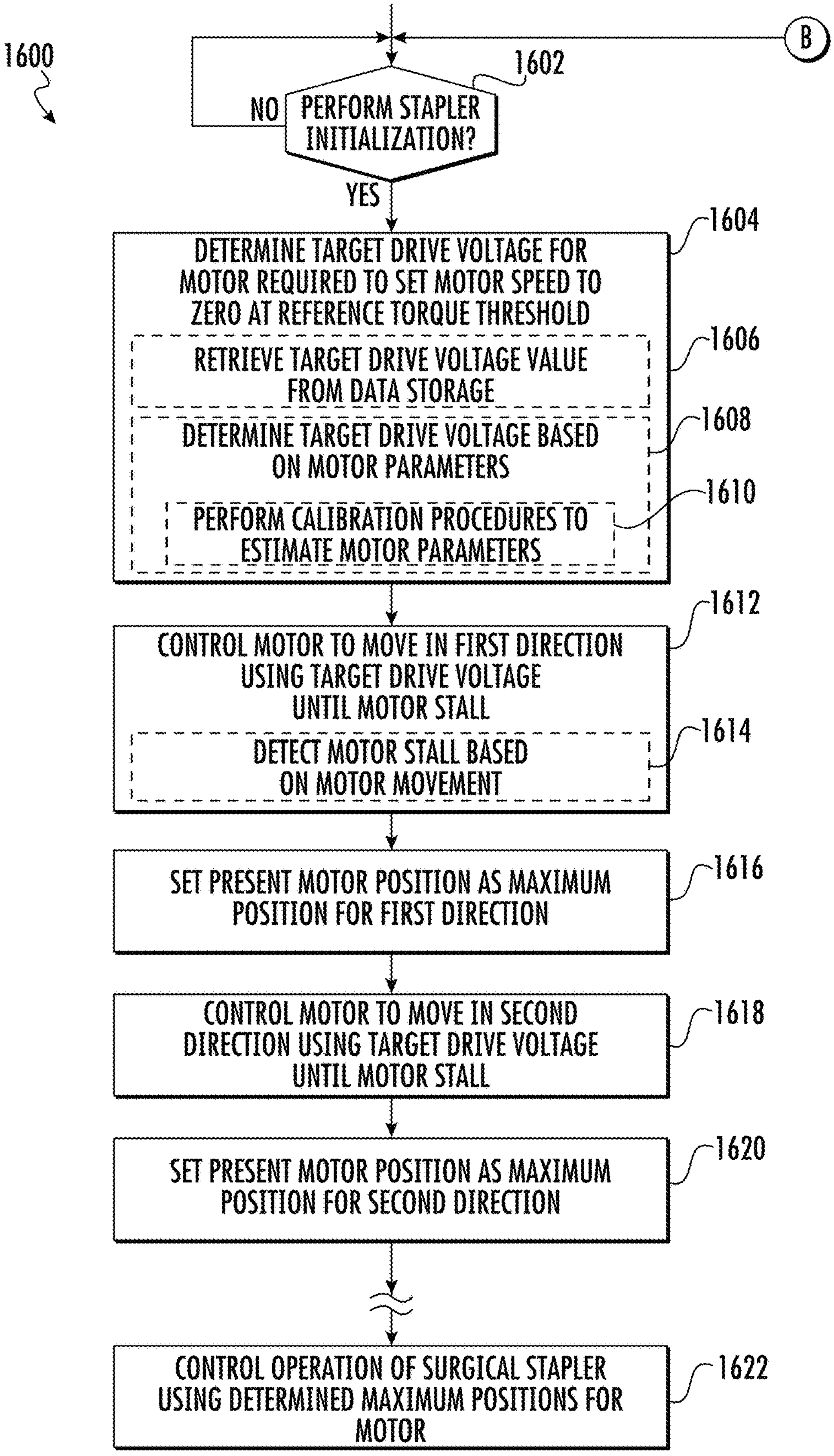

FIG. 16

TECHNOLOGIES FOR HOMING A MOTOR OF A SURGICAL STAPLER

TECHNICAL FIELD

The present disclosure relates generally to surgical instruments and, more particularly, to surgical stapling and cutting instruments and associated staple cartridges for use with the surgical instruments to facilitate the cutting and stapling of patient tissue.

BACKGROUND

Surgical procedures often involve the use of various surgical instruments to assist a surgeon in the performance of the corresponding procedure. Recently, minimally invasive surgical (MIS) instruments have gained preference over traditional "open" surgical devices as the use of MIS instruments can reduce post-operative recovery time and associated tissue scarring. Endoscopy and laparoscopy are common types of MIS procedures in which a tube or trocar is inserted into natural or surgically-made openings (e.g., incisions) of the patient, depending on the particular procedure. The tube or trocar is then used to facilitate introduction of associated surgical instruments into the patient's body (e.g., the patient's abdominal cavity) to treat internal tissue of the patient.

One type of surgical instrument usable in MIS procedures is a surgical stapler, sometimes referred to as an "endocutter." A typical surgical stapler includes an elongated shaft to facilitate use of a trocar and an end effector located at a distal end of the elongated shaft. The elongated shaft facilitates the use of the surgical stapler with a trocar to access the patient's anatomical environment (e.g., the patient's abdominal cavity) and may include one or more articulation joints to increase the usability of the surgical stapler in the anatomical environment. Similarly, the end effector may be attached to the elongated shaft via an articulation joint to allow the end effector to be positioned as desired by the surgeon. A typical end effector of a surgical stapler includes a pair of jaws movable between an open position and a closed position to facilitate the grasping of tissue within the jaws. One of the jaws is embodied as a cartridge jaw and is configured to receive a staple cartridge, and the other jaw is embodied as an anvil jaw configured to provide a surface on which the staples are formed. The end effector also includes a cutting element (typically referred to as a "knife"), which is translated distally along the end effector during a firing phase of the surgical stapler to transect tissue presently grasped by the end effector. As the knife advances along the end effector, staples contained in the staple cartridge are progressively ejected to thereby seal opposing sides of the transected tissue.

Surgical staplers may be embodied as independent, handheld devices or configured to be coupled to a robotic surgery system. In hand-held embodiments, the surgical stapler may include a handle and an associated trigger, which is operable by a surgeon to control the end effector and the ejection of the staples from the staple cartridge. In robotic embodiments, the surgical stapler is configured to be mounted to a robotic arm of a robotic manipulator, which is controllable by the surgeon via a remote control console. For example, the control console may include various input devices that can be grasped and manipulated by the surgeon to cause movement and firing of the surgical stapler.

Typical surgical staplers, including some robotic surgical staplers, include various motors to control movement and operation of the surgical stapler. Some of those motors may be configured to contact physical hardstops to limit or restrict further movement of the motor (e.g., a rotational hardstop that limits further rotation of the motor). Engagement of those hardstops by the motor is typically inferred based on proxy signals such as motor torque and voltage (e.g., an abrupt increase in motor torque may be indicative of contact with the hardstop), rather than based on the actual movement or position of the motor.

SUMMARY

According to an aspect of the present disclosure, a robotic surgical system may include a robotic surgical stapler, a robotic arm, and a control system. The robotic surgical stapler may include a drive housing, an elongated shaft extending from the drive housing, an end effector located at a distal end of the elongated shaft, and a gear assembly located in the drive housing and configured to control movement of the end effector. The gear assembly may include a drive gear having a rotation limiter configured to contact a rotation hardstop to limit rotation of the diver gear. The robotic arm may include a motor operably coupled to the gear assembly of the robotic surgical stapler and configured to rotate the drive gear to control movement of the end effector. The control system may be configured to control operation of the motor to control movement of the end effector. The control system may be further configured to determine a target drive voltage for the motor, wherein the target drive voltage is configured to set a speed of the motor to zero at a reference torque threshold, control the motor to rotate in a first direction using the target drive voltage until the motor stalls, wherein the stalling of the motor is indicative of contact between the rotation limiter of the gear assembly and the rotation hardstop, determine, in response to the stalling of the motor in response to rotation in the first direction, a first position of the motor, and set the first position of the motor as a maximum motor position for the first direction.

In some embodiments, to control the motor to rotate in the first direction using the target drive voltage until the motor stalls may include monitoring movement of the motor while rotating the motor in the first direction, and determining that the motor has stalled in response to detecting that the motor has stopped moving. Additionally, in some embodiments, the control system may be further configured to control the motor to rotate in a second direction, opposite the first direction, using the target drive voltage until the motor stalls; determine, in response to the stalling of the motor in response to rotation in the second direction, a second position of the motor; and set the second position of the motor as a maximum motor position for the second direction.

Additionally, in some embodiments, to determine the target drive voltage may include to retrieve the target drive voltage from a data storage. Additionally or alternatively, to determine the target drive voltage may include to determine the target drive voltage based on motor parameters of the motor. For example, in some embodiments, the control may be further configured to perform a calibration process to estimate the motor parameters of the motor.

In some embodiments, to determine the target drive voltage may include to determine a nominal stall torque of the motor; determine a nominal free-load speed of the motor; determine a nominal drive voltage of the motor; determine the reference torque threshold for the motor based on a physical property of the rotation limiter and the rotation hardstop; and determine the target drive voltage that sets the speed of the motor to zero at the reference torque threshold based on the nominal stall torque, the nominal free-load speed, and the nominal drive voltage of the motor. For example, to determine the target drive voltage may include to determine the target drive voltage according to the following equation: $S_{motor}=((V_{target}/V_{nom})*S_{free})-(S_{free}/T_{stall})*T_{ref}$, wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold. Additionally, in some embodiments, the control system may be further configured to determine an efficiency of the motor and adjust the target drive voltage based on the efficiency.

Additionally, in some embodiments, in the robotic arm may include an arm interface having a puck driver controlled by the motor. The gear assembly of the surgical stapler further may include an input puck configured to mate with the puck driver to transfer rotational movement from the puck driver to the drive gear. In some embodiments, the gear assembly may further include a worm gear operatively coupled to the input puck and meshed with the drive gear. Additionally, in some embodiments, the control system may be further configured to control operation of the surgical stapler to perform a surgical procedure using the maximum motor position for the first direction and the second direction.

According to another aspect of the present disclosure, a method for homing a motor of a surgical stapler system may include determining, by a control system, a target drive voltage for the motor, wherein the target drive voltage is configured to set a speed of the motor to zero at a reference torque threshold; controlling, by the control system, the motor to rotate in a first direction using the target drive voltage; monitoring, by the control system, movement of the motor while the motor is rotated in the first direction; determining, by the control system, that the motor has stalled in response to a determination that the motor has stopped moving; determining, by the control system and in response to the stalling of the motor, a first position of the motor, and setting, by the control system, the first position of the motor as a maximum motor position for the first direction.

In some embodiments, the method may further include controlling, by the control system, the motor to rotate in a second direction, opposite the first direction, using the target drive voltage until the motor stalls; determining, by the control system and in response to the stalling of the motor in response to rotation in the second direction, a second position of the motor; and setting, by the control system, the second position of the motor as a maximum motor position for the second direction.

Additionally, in some embodiments, determining the target drive voltage includes determining the target drive voltage based on motor parameters of the motor. For example, the method may include performing, by the control system, a calibration process to estimate the motor parameters of the motor.

In some embodiments, determining the target drive voltage may include determining, by the control system, a nominal stall torque of the motor; determining, by the control system, a nominal free-load speed of the motor; determining, by the control system, a nominal drive voltage of the motor; determining, by the control system, the reference torque threshold for the motor based on a physical property of the rotation limiter and the rotation hardstop; and determining, by the control system, the target drive voltage that sets the speed of the motor to zero at the reference torque threshold based on the nominal stall torque, the nominal free-load speed, and the nominal drive voltage of the motor. For example, determining the target drive voltage may include determining the target drive voltage according to the following $S_{motor}=((V_{target}/V_{nom})*S_{free})-(S_{free}/T_{stall})*T_{ref}$, wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

Additionally, in some embodiments, the method may further include determining, by the control system, an efficiency of the motor and adjust the target drive voltage based on the efficiency. Furthermore, in some embodiments, the method may include controlling, by the control system, operation of the surgical stapler to perform a surgical procedure using the maximum motor position for the first direction and the second direction.

BRIEF DESCRIPTION OF THE DRAWINGS

The detailed description particularly refers to the following figures, in which:

FIG. 16 is a simplified flow diagram of a method for homing a motor of a surgical stapler system, which may be executed by the control system of FIG. 11;

DETAILED DESCRIPTION OF THE DRAWINGS

Figure 1:
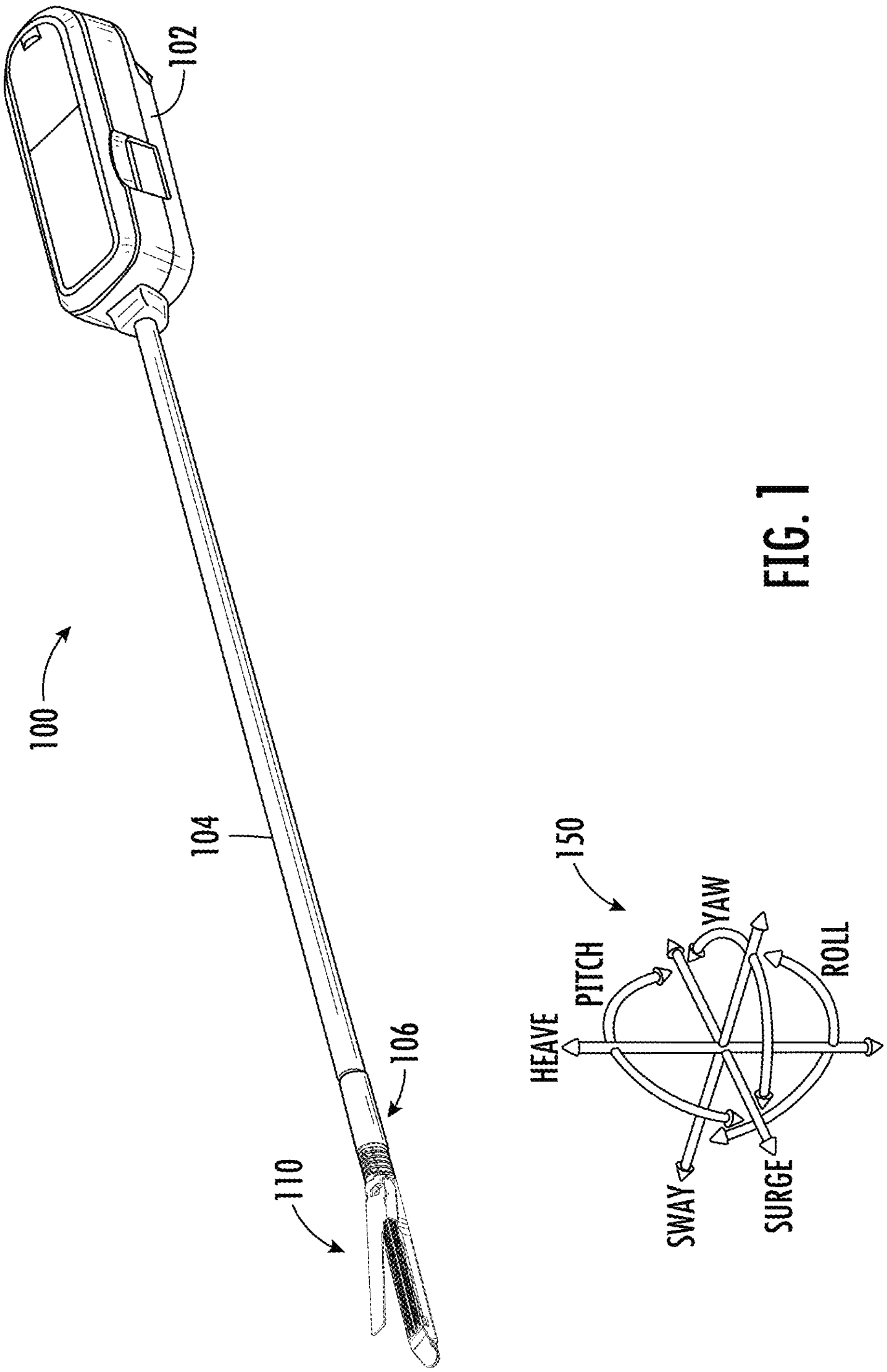
FIG. 1 is a perspective view of an embodiment of a surgical stapler configured for use with a robotic surgical system.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, et cetera, may be used throughout the specification in reference to the surgical instruments described herein as well as in reference to the patient's natural anatomy. Such terms have well-understood meanings in both the study of anatomy and the field of surgery. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

Portions of the disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a surgical stapler or "endocutter" 100 is configured for use in minimally invasive surgery (MIS) procedures including, but not limited to, endoscopic and laparoscopic procedures. The surgical stapler 100 is configured to contemporaneously transect and staple tissue during the performance of such surgical procedures. Although the concepts presented below are described in regard to a surgical stapler, it should be appreciated that the presented concepts may be applicable to other types of surgical instruments configured to perform different surgical functions including, but not limited to, surgical scissors, tissue graspers, energy-based surgical instruments, clip appliers, needle drivers, and/or other surgical instruments.

The illustrative surgical stapler 100 includes a drive housing 102, an elongated shaft 104 that extends distally away from the drive housing 102, and an end effector 110 located at a distal end of the elongated shaft 104 opposite the drive housing 102. As discussed in more detail below, the surgical stapler 100 is embodied as a robotic surgical stapler and is configured to be used with a corresponding robotic surgical system. As such, the drive housing 102 includes coupling features that that facilitate the mounting of the drive housing 102 to a robotic arm of a robotic manipulator of the robotic surgery system as discussed below in regard to FIGS. 8 and 9. The mounting of the drive housing 102 to the robotic arm allows the robotic manipulator to control various functions of the surgical stapler 100, including the movement and "firing" of the end effector 110, as discussed in more detail below.

The elongated shaft 104 is sized and configured for use in minimally invasive surgery procedures. For example, the elongated shaft 104 has a length and diameter that is sized to allow the elongated shaft 104 to be inserted into a trocar or similar surgical tube to allow positioning of the end effector 110 into the patient's anatomical environment (e.g., the patient's abdominal cavity). Illustratively, the distal end of the elongated shaft 104 is coupled to the end effector 110 via an articulable joint 106, which allows the end effector 110 to be moved to different orientations and/or positions relative to the elongated shaft 104.

In the illustrative embodiment, the articulable joint 106 provides six degrees of freedom to the end effector 110. For example, as indicated by coordinate frame 150, the degrees of freedom of the end effector 110 may include three translational degrees (i.e., surge, heave, and sway) and three rotational degrees (i.e., roll, pitch, and yaw). The "surge" degree of freedom refers to forward and backward translational movement of the end effector 110 relative to the elongated shaft 104, the "heave" degree of freedom refers to upward and downward translational movement of the end effector 110 relative to the elongated shaft 104, and the "sway" degree of freedom refers to left and right translational movement of the end effector 110 relative to the elongated shaft 104. The "roll" degree of freedom refers to rotation of the end effector 110 along a longitudinal axis defined by the end effector 110, the "pitch" degree of freedom refers to upward and downward tilting of the end effector 110 relative to the elongated shaft 104, and the "yaw" degree of freedom refers to leftward or rightward turning of the distal end of the end effector 110 relative to the elongated shaft 104.

The elongated shaft 104 also houses a portion of an actuation system (not shown) to control the movement and activation (e.g., the "firing") of the end effector 110. The actuation system may include various articulation cables, push rods, firing rods, and/or other devices, which extend through the elongated shaft 104 from mechanisms located in the drive housing 102 to components of the articulable joint 106 and/or the end effector 110. In this way, the drive housing 102 is configured to control the movement and activation (i.e., the "firing") of the end effector 110.

Figure 2:
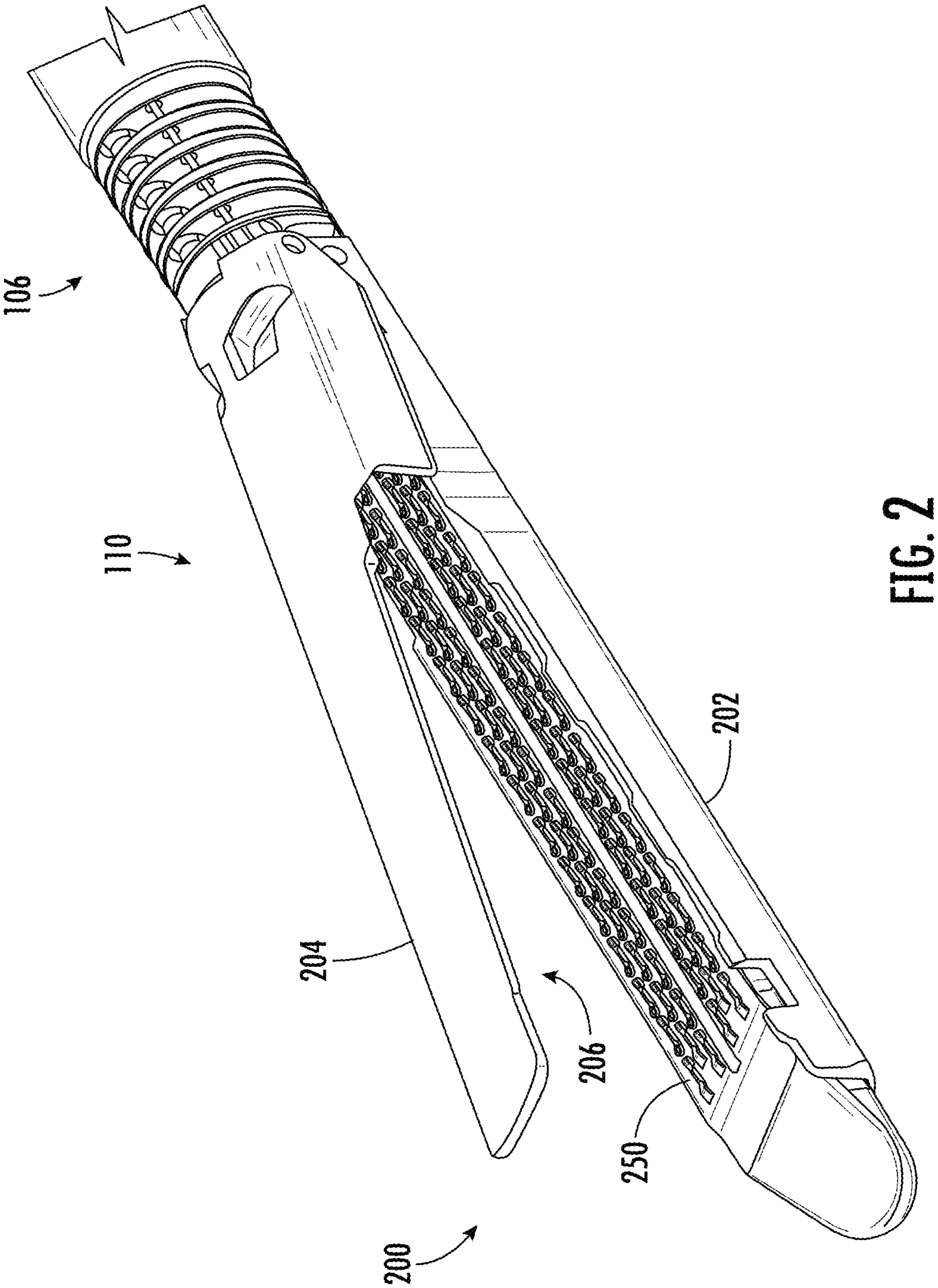
FIG. 2 is a perspective view of an embodiment of an end effector of the surgical stapler of FIG. 1.

Referring now to FIG. 2, the end effector 110 includes a jaw assembly 200, which illustratively includes a pair of jaws 202, 204 that oppose each other. The jaw 202 is illustratively embodied as a "cartridge" jaw and includes a channel 300 (see FIG. 3) configured to receive a staple cartridge 250. The jaw 204 is illustratively embodied as an "anvil" jaw and includes a bottom surface 206 having forming pockets configured to deform staples ejected from the staple cartridge 250.

The jaw assembly 200 is movable between an open state in which the anvil jaw 204 is positioned away from the cartridge jaw 202 and a closed state in which the anvil jaw 204 is positioned near or otherwise contacts the cartridge jaw 202. Illustratively, the anvil jaw 204 is configured to move toward and away from the cartridge jaw 202. However, in other embodiments, the cartridge jaw 202 may be configured to move relative to the anvil jaw 204 or both jaws 202, 204 may be configured to move toward or away from each other. Additionally, it should be appreciated that the open state may correspond to a degree of openness that is less than a fully opened position of the jaw assembly 200 and the closed state may correspond to a degree of closeness that is less than a fully closed position. That is, the closed state may, for example correspond to a minimal distance between the distal ends of the cartridge jaw 202 and the anvil jaw 204 and the open state may correspond to a maximum distance between the distal ends of the jaws 202, 204. However, in other embodiments, the open state may correspond to a fully opened position of the jaw assembly 200 and the closed state may correspond to a fully closed position of the jaw assembly 200.

Figure 3:
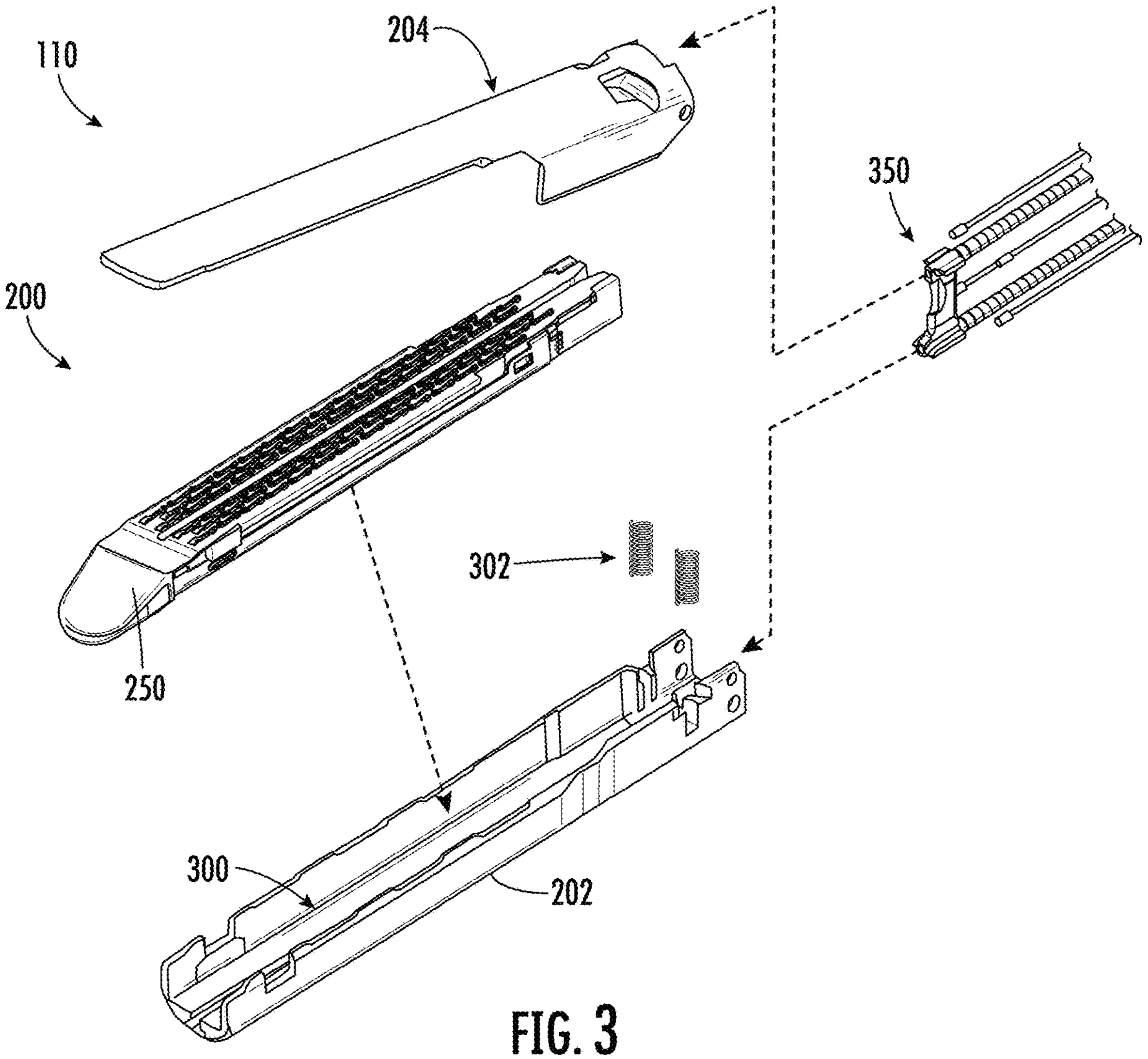
FIG. 3 is an exploded perspective view of and embodiment of a distal end of the surgical stapler of FIG. 1, including the end effector of FIG. 2.

As shown in FIG. 3, the jaw assembly 200 is biased in the open state by a pair of springs 302. That is, the springs 302 bias the anvil jaw 204 away from the cartridge jaw 202. However, actuation of the jaw assembly 200 overcomes the biasing force of the springs 302 to move the jaw assembly 200 from the open state to the closed state. When in the closed state, the end effector 110 can be "fired" to effect the cutting and stapling of tissue held within the jaw assembly 200.

The end effector 110 also includes an I-beam 350, which is configured to translate forward during the firing of the end effector 110 from the proximal end of the jaws 202 toward the distal end of the jaws 202, 204. To do so, portions of the I-beam 350 are received in corresponding channels of the cartridge jaw 202 and the anvil jaw 204 as discussed in more detail below in regard to FIGS. 4 and 5. When the end effector 110 is fired, the I-beam 350 translates forward within the channels of the jaws 202, 204. The forward movement of the I-beam 350 may cause the anvil jaw 204 to move further downward toward or against the cartridge jaw 202 and clamp the jaw assembly in the closed state.

Figure 5:
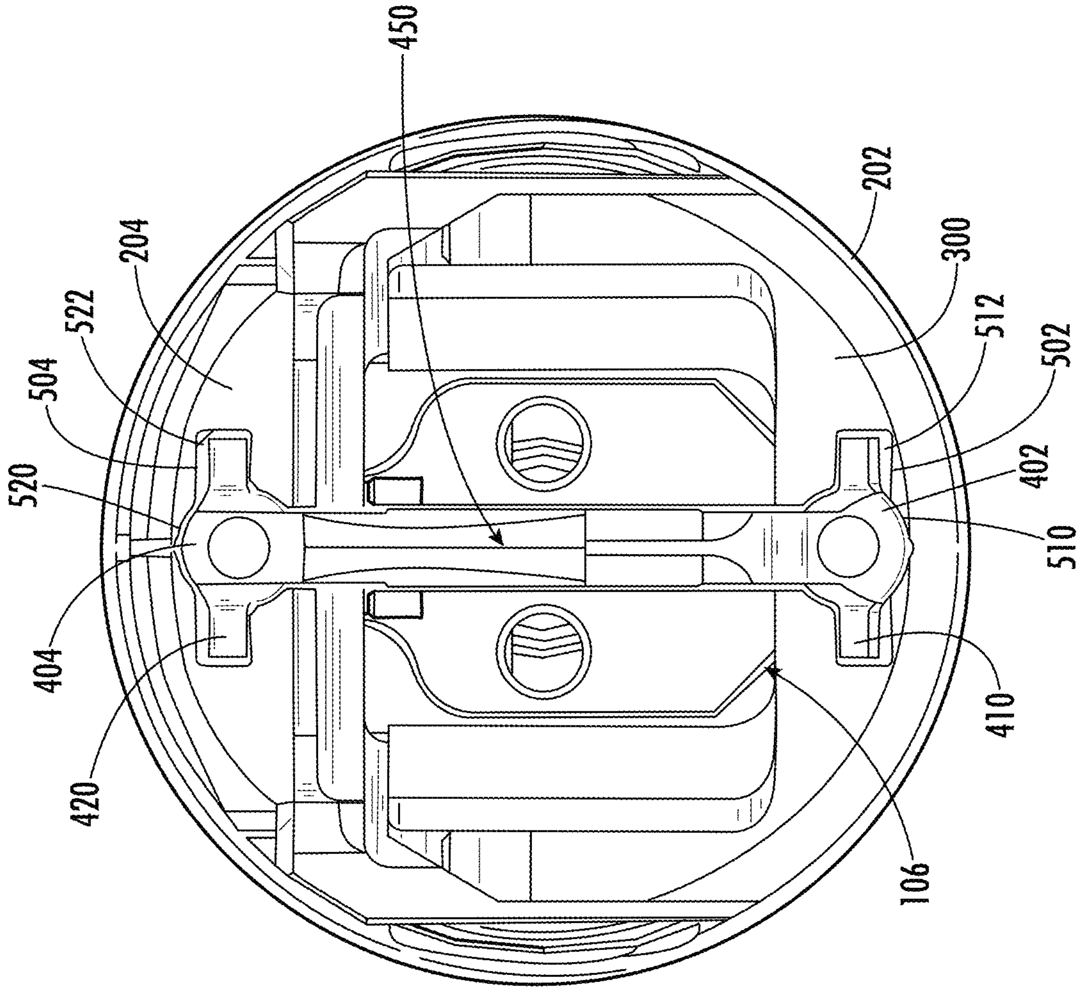
FIG. 5 is a cross-sectional view of the end effector of FIG. 1 in a closed state and showing the I-beam, of FIG. 4 received in corresponding channels of the end effector of FIG. 2 with the knife of the I-beam extending between the corresponding channels.
Figure 4:
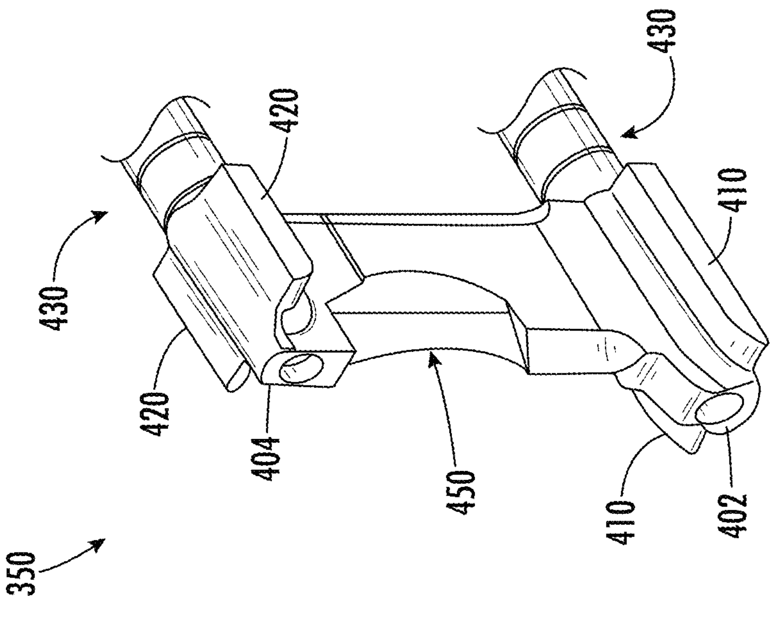
FIG. 4 is a perspective view of an embodiment of an I-beam of the end effector of FIG. 2, which includes a knife.

Referring now to FIGS. 4 and 5, the I-beam 350 includes a lower base 402, an upper base 404, and a knife 450 located between the upper and lower bases 402, 404. A pair of lower wings 410 extend laterally outward from the lower base 402. Similarly, a pair of upper wings 420 extend laterally outward from the upper base 404. A push rod 430 is coupled to each of the bases 402, 404 and to control mechanisms located in the drive housing 102. The control mechanisms of the drive housing 102 control movement of the push rods 430, which moves the I-beam 350 forward and backward within the jaw assembly 200.

When the end effector 110 is fired, the I-beam 350 moves within a lower I-beam channel 502 of the cartridge jaw 202 and an upper I-beam channel 504 of the anvil jaw 204 as shown in FIG. 5. The I-beam channel 502 of the cartridge jaw 202 includes a base channel 510 and a pair of wing channels 512, which are open to and in fluid communication with the base channel 510 and extend laterally outward therefrom. The lower base 402 of the I-beam 350 is received in and moves within the base channel 510 of the I-beam channel 502. Similarly, each lower wing 410 is received in and moves within a corresponding one of the wing channels 512. The I-beam channel 504 of the anvil jaw 204 also includes a base channel 520 and a pair of wing channels 522, which are open to and in fluid communication with the base channel 520 and extend laterally outward therefrom. The upper base 404 of the I-beam d 350 is received in and moves within the base channel 520 of the I-beam channel 502. Similarly, each upper wing 420 is received in and moves within a corresponding one of the wing channels 522.

Figure 6:
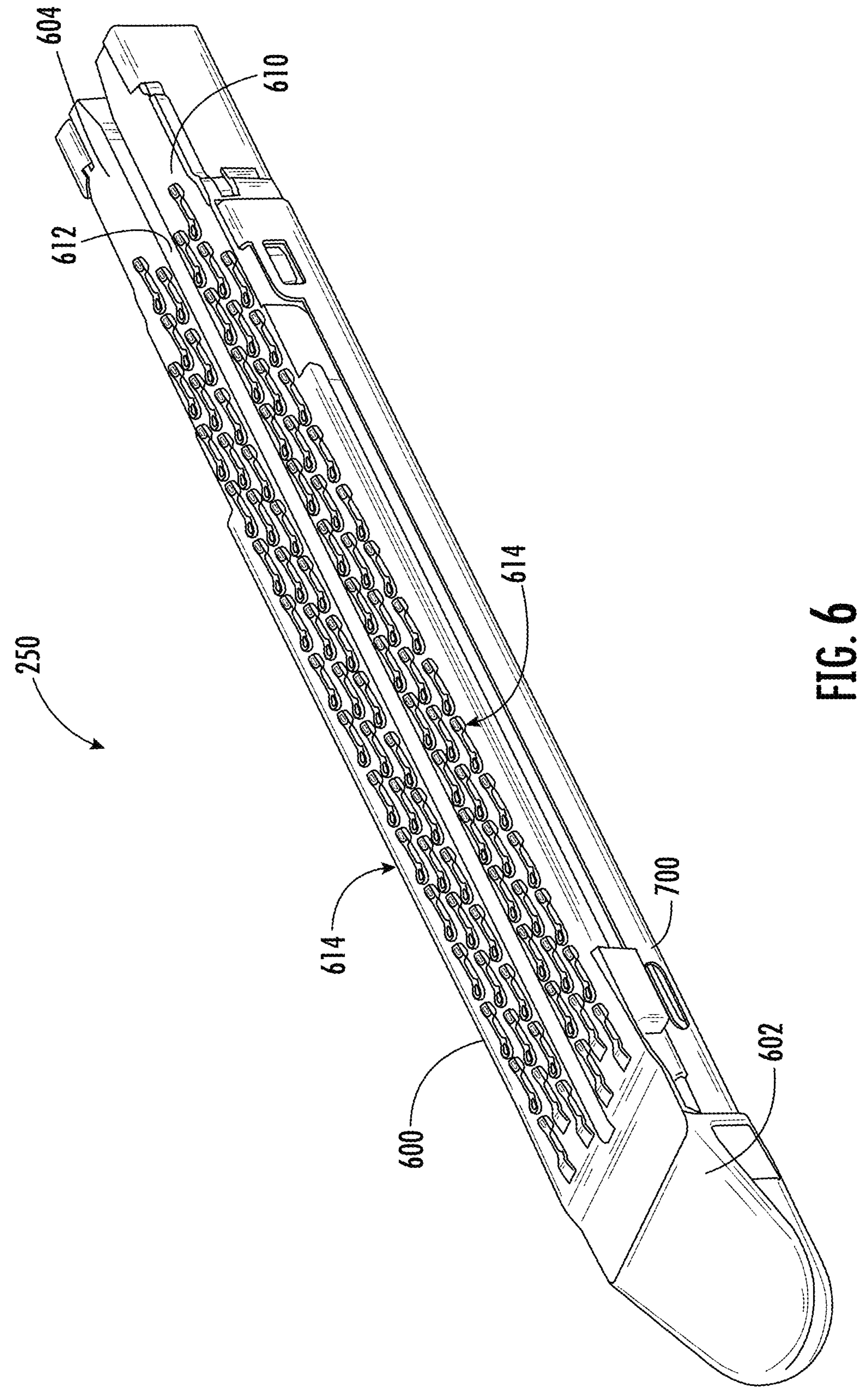
FIG. 6 is a perspective view of an embodiment of a staple cartridge that may be inserted into the end effector of FIG. 2.
Figure 7:
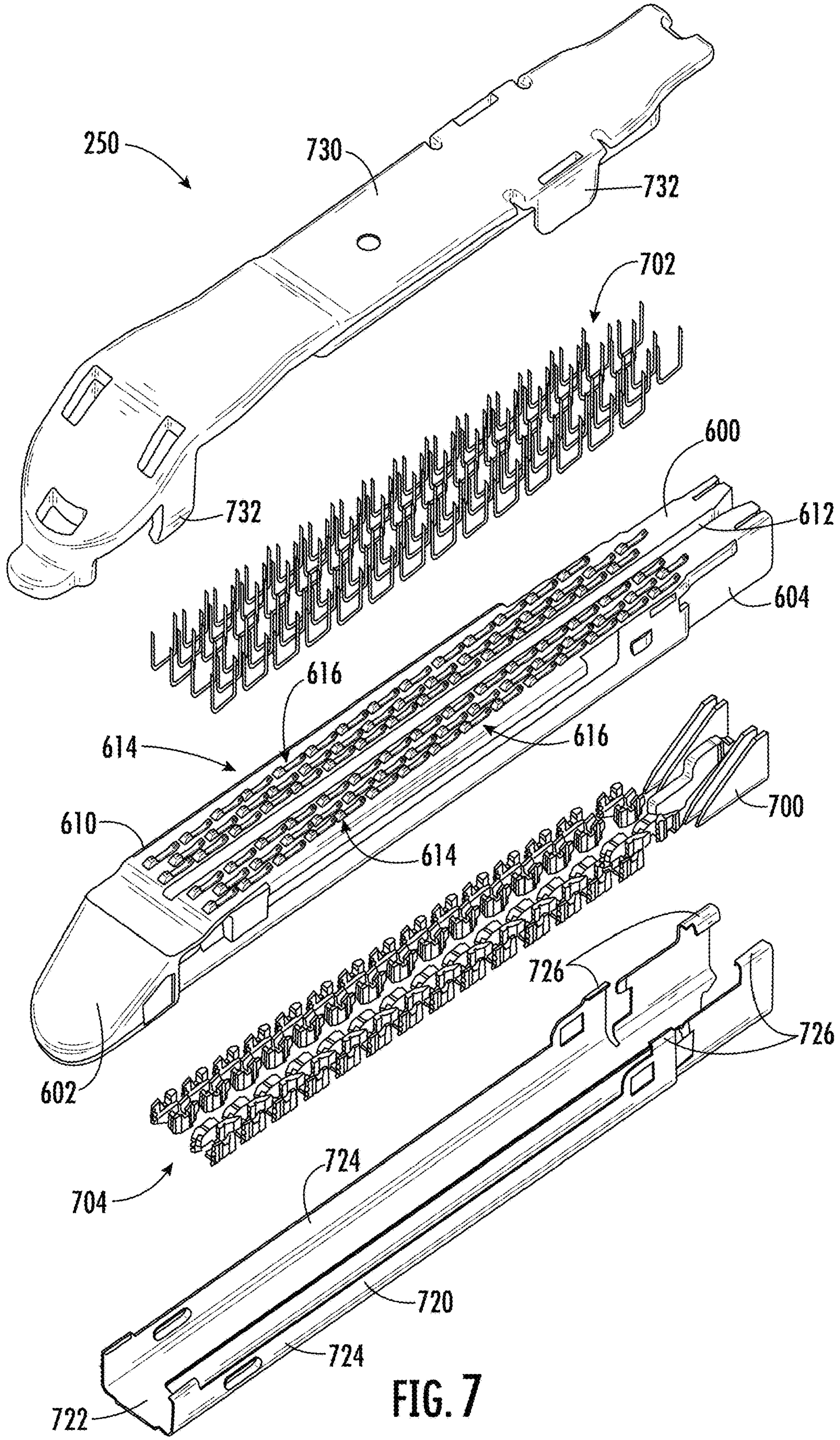
FIG. 7 is an exploded, perspective view of the staple cartridge of FIG. 6.

Referring now to FIGS. 6 and 7, the illustrative staple cartridge 250 includes a cartridge body 600 having a distal end 602 and a proximal end 604. The cartridge body 600 also includes a deck 610 that extends from the proximal end 604 to the distal end 602. The deck 610 includes a longitudinal knife slot 612 that is located centrally on the deck 610 and extends from the distal end 602 toward the proximal end 604 of the cartridge body 600. During a firing stroke of the surgical stapler 100 (i.e., when the end effector is "fired"), the I-beam 350 transversed along the longitudinal knife slot 612 with the knife 450 of the I-beam 350 protruding upwardly from the longitudinal knife slot 612 to facilitate the transection of tissue captured within in the end effector 110 and held between the staple cartridge 250 and the anvil jaw 204.

A set of staple cavities 614 are defined in the deck 610 on either side of the longitudinal knife slot 612. A staple 702 is positioned in each of the staple cavities 614 and is supported by a corresponding staple driver 704. The staple cartridge 250 also includes a staple sled 700, which is initially located toward the proximal end 604 of the cartridge body 600 and is pushed toward the distal end 602 by the I-beam 350 when the end effector 110 is fired. The staple sled 700 lifts each staple driver 704 when the sled 700 comes into contact with the corresponding staple driver 704, which ejects the staple 702 associated with the corresponding staple driver 704 from the corresponding staple cavity 614. In the illustrative embodiment, the deck 610 includes staple guides or projections 616 that project upwardly from the deck 610 around each staple cavity 614. The staple guides 616 are configured to guide or control the legs of the staples 702 as the staples 702 are being ejected from the staple cavities 614. Illustratively, the staple guides 616 are located around the distal and proximal ends of each staple cavity 614, but may completely surround each staple cavity 614 or be located on only one end of each staple cavity 614 in other embodiments. The staple guides 616 may also form a set of "teeth" and be configured to grasp tissue held within the jaw assembly 200 to restrict movement of the tissue. In other embodiments, the deck 610 of the cartridge body 600 maybe devoid of any staple guides 616.

The staple cartridge 250 also includes a pan 720, which is attached to the cartridge body 600 and is configured to retain the staple drivers 704 and associated staples 702 within the cartridge body 600. Illustratively, the pan 720 is formed from a metallic material and includes a floor 722 and a pair of sidewalls 724 that extend upwardly from the floor 722 and wrap onto the sides of the cartridge body 600. The pan 720 includes a set of attachment tabs 726 that are configured to secure the pan 720 to the cartridge body 600.

Prior to use, the staple cartridge 250 includes a cover 730 attached to the cartridge body 600. The cover 730 is configured to cover the deck 610 of the staple cartridge 250 and includes a set of attachment tabs 732 configured to secure the cover 730 to the cartridge body 600. To prepare the staple cartridge 250 for use in the end effector 110, the cover 730 is removed from the cartridge body 600.

Although not illustrated in FIGS. 6 and 7, the staple cartridge 250 may also include one or more electronic circuits or devices configured to perform one or more associated functions. For example, such electronic circuitry may include processors, digital storage devices, communication circuitry, sensor circuitry, and/or other electrical components.

Figure 8:
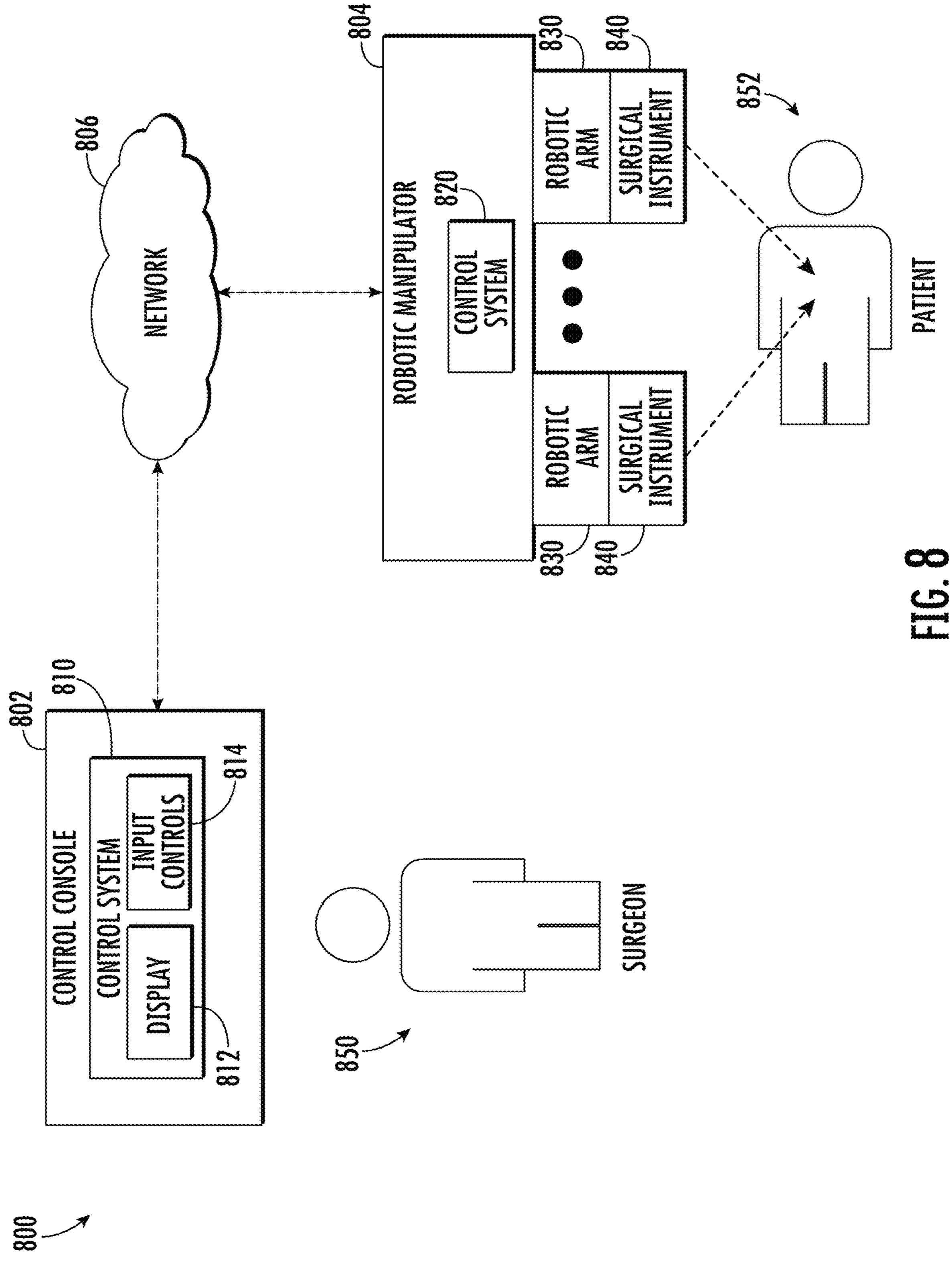
FIG. 8 is a simplified block diagram of an embodiment of a robotic surgical system including a control console and a robotic manipulator, with which the surgical stapler of FIG. 1 may be used.

Referring now to FIG. 8, as discussed above, the illustrative surgical stapler 100 is configured for use with a corresponding robotic surgical system 800. The robotic surgical system 800 includes a control console 802 and a robotic manipulator 804, which communicate with each other over a communication network 806. Although only a single control console 802 and a single robotic manipulator 804 is shown in FIG. 8, it should be appreciated that the robotic surgical system 800 may include additional control consoles 802 and/or robotic manipulators 804 in other embodiments.

The control console 802 is usable by a surgeon 850 to control the operation of the robotic manipulator 804. To do so, the control console 802 includes a control system 810. Illustratively, the control system 810 includes a display 812 and one or more input controls 814. However, it should be appreciated that the control system 810 may include additional electrical components and devices, such as a processor, a memory, and a communication subsystem to enable communications of the components of the control system 810, which are not illustrated in FIG. 8 for clarity.

The display 812 may be embodied as any type of display device capable of generating images viewable by the surgeon 850. In use, the display 812 may display images related to the surgical procedure being performed via the robotic manipulator 804. The displayed images may be obtained from, for example, an endoscopic camera operated by the robotic manipulator 804. Additionally, the display 812 may display information, including data determined by the control console 802 and/or the robotic manipulator 804, related to the surgical procedure (e.g., positional data of the robotic manipulator 804).

The input controls 814 are usable by the surgeon 850 to control the functionality of the robotic manipulator 804. The input controls 814 may be embodied as any type of input device capable of receiving a corresponding input from the surgeon 850. For example, the input controls 814 may include physical controllers, such as joy sticks, hand-held actuator modules, exoskeletal gloves, and/or other input devices. The input controls 814 may also include input devices other than hand-controlled devices such as foot pedals, vision tracking modules, and/or the like. In many embodiments, the input controls 814 are movable in multiple degrees of freedom to control the positioning and operation of the robotic manipulator 804.

The robotic manipulator 804 also includes a control system 820 and one or more robotic arms 830 to which surgical instruments 840 (e.g., the surgical stapler 100) may be mounted. In some embodiments, the robotic manipulator 804 may be mounted to a transport cart, sometimes referred to as an "arm cart," that enables mobility of the robotic manipulator 804 and the associated robotic arms 830.

The robotic arms 830 may include various articulable linkages and associated motors, which are controllable by the control console 802 to move the corresponding robotic arm 830 and any associated surgical instrument 840 to a desired position. For example, by manipulating an input control 814 of the control console 802, the surgeon 850 may control the positioning of a corresponding robotic arm 830, as well as the functionality of the associated surgical instrument 840 (e.g., the firing of the surgical stapler 100).

The control system 820 may be embodied as any type of controller or control circuit capable of controlling the functionality of the robotic manipulator including, for example, the movement of the robotic arms 830 and the activation of the surgical instruments 840 based on control signals received from the control console 802. To do so, the control system 820 may include various electrical components, circuits, and/or devices, such as a processor, a memory, and a communication subsystem to enable communications of the components of the control system 820, which are not illustrated in FIG. 8 for clarity.

In use, the robotic manipulator 804 is positioned in close proximity to a patient 852 requiring surgery. The robotic manipulator 804 may be locked or mounted in place for the duration of the surgery. The surgeon 850 may then manipulate the input controls 814 to position one or more robotic arms 830 and associated surgical instruments 840 into a desired position. For example, the surgeon 850 may position a robotic arm 830 such that an associated surgical instrument 840 is inserted through a trocar or similar elongated passageway into the anatomical environment (e.g., the abdominal cavity of the patient 852). Once so positioned, some surgical instruments 840 (e.g., an endoscope) may be locked into position to avoid unintended repositioning.

The network 806 may be embodied as any type of wired and/or wireless network or set of communication links capable of facilitating communications between the control console 802 and the robotic manipulator 804. To do so, the network 806 enable such communications using any suitable data communication specification and/or protocol. As such, in some embodiments, the network 806 may include additional devices, such as additional computers, routers, stations, and/or switches, to facilitate such communications between the control console 802 and the robotic manipulator 804.

Figure 9:
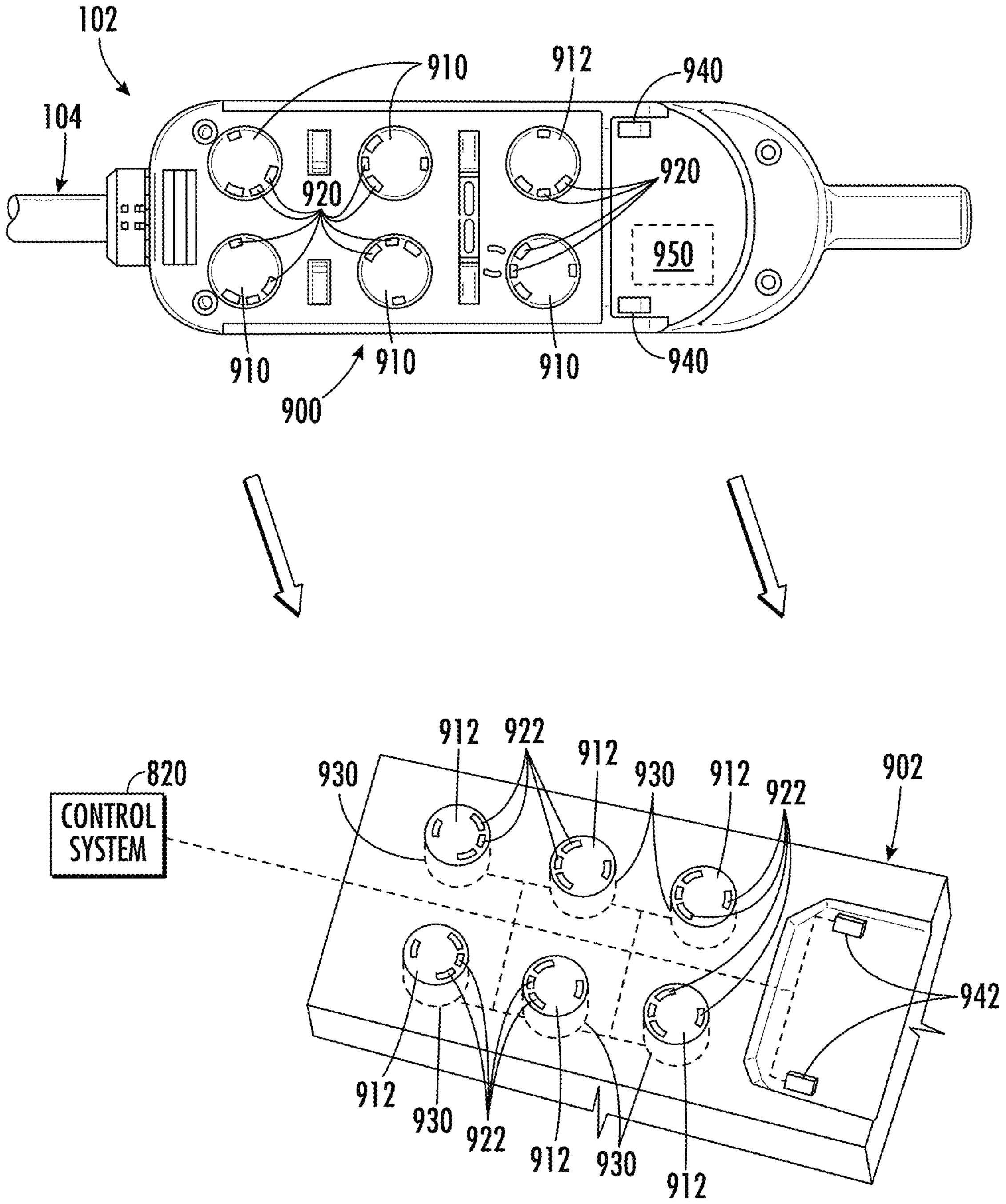
FIG. 9 is a diagrammatic view of an embodiment of a tool interface located on a bottom side of a drive housing of the surgical stapler of FIG. 1 being coupled to an arm interface located on a robotic arm of the robotic manipulator of the robotic surgical system of FIG. 8.

Referring now to FIG. 9, as discussed above, the surgical stapler 100 (and other surgical instruments 840) is configured to be mounted to a robotic arm 830 of the robotic manipulator 804. To facilitate such mounting, the drive housing 102 of the surgical stapler 100 includes a tool interface 900 located on a bottom side of the drive housing 102. The tool interface 900 is configured to mate with an arm interface 902 of the corresponding robotic arm 830 to couple the surgical stapler 100 to the robotic arm 830. The coupling of the surgical stapler 100 to the robotic arm 830 may be further facilitated via various mechanical, magnetic, and/or electrical features. In some embodiments, a sterile barrier may also be used between the surgical stapler 100 and the robotic arm 830. It should be appreciated that mounting the surgical stapler 100 to the robotic arm places the surgical stapler 100 into communication and under the control of the control system 820 of the robotic manipulator 804, which is controlled by the control console 802 as discussed above.

The tool interface 900 includes a set of input pucks 910, which are manipulable to control functions of the surgical stapler 100 such as the positioning and firing of the end effector 110. Each input puck 910 is configured to mate with a corresponding puck driver 912 of the arm interface 902. To do so, each input puck 910 includes mating features 920 that are configured to mate with mating features 922 of the corresponding puck driver 912. In the illustrative embodiment, the mating features 920 of the input pucks 910 are embodied as tabs or protrusions that extend upwardly from the corresponding input puck 910, and the mating features 922 of the puck drivers 912 are embodied as recesses configured to receive the tabs/protrusions 920 of the input pucks 910. In other embodiments, however, the mating features 920 of the input pucks 910 may be embodied as recesses and the mating features 922 of the puck drivers 912 may be embodied as tabs/protrusions.

The arm interface 902 includes an electric motor 930 operatively coupled to each puck driver 912. Each electric motor 930 is communicatively coupled to and controlled by the control system 820. Actuation of a given electric motor 930 causes actuation of the associated puck driver 912, which causes actuation of the corresponding input puck 910. For example, rotation of an electric motor 930 causes rotation of the associated puck driver 912, which causes rotation of the corresponding input puck 910. In this way, the positioning and activation (e.g., "firing") of the end effector 110 of the surgical stapler 100 may be controlled via actuation of the puck drivers 912 and associated input pucks 910.

The tool interface 900 also includes a set of electrical connectors 940, which are configured to mate with corresponding electrical connectors 942 of the arm interface 902. The electrical connectors 940, 942 provide electrical communication between the surgical stapler 100 and the robotic manipulator 804. However, in other embodiments, the surgical stapler 100 and the robotic manipulator 804 may be configured to communicate in other ways, such as via wireless communications. In some embodiments, the tool interface 900 may also include a control system 950. In such embodiments, the control system 950 may be configured to control and/or monitor various operations the surgical stapler 100. The control system 950 may include various electrical components, circuits, and/or devices, such as a processor, a memory, and a communication subsystem to enable communications of the components of the control system 950, which are not illustrated in FIG. 9 for clarity.

Figure 10:
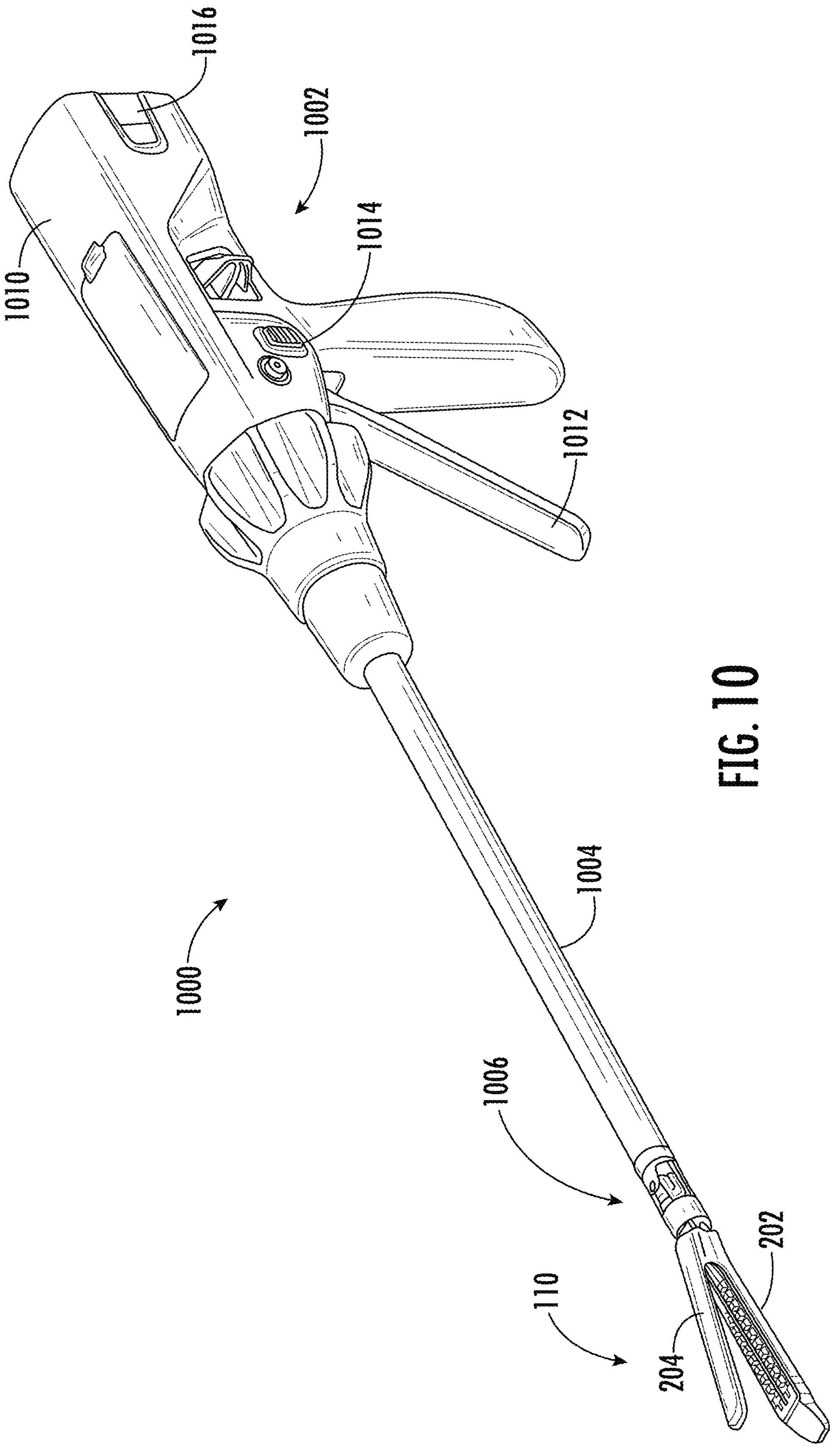
FIG. 10 is a perspective view of an embodiment of a hand-held surgical stapler including the end effector of FIG. 2.

Although the illustrative surgical stapler 100 shown and described above in regard to FIGS. 1-9 is configured for use in a robotic surgical system, the features and concepts of the surgical stapler 100 described above and below may be applicable to hand-held surgical staplers and devices. For example, as shown in FIG. 10, the end effector 110 may be incorporated into a hand-held surgical stapler 1000. The surgical stapler 1000 includes a handle 1002 and an elongated shaft 1004 extending from the handle 1002. The distal end of the elongated shaft 1004 is coupled to the end effector 110 via an articulable joint 1006, which may be substantially similar to the articulable joint 106 described above.

The handle 1002 includes a handle housing 1010 and a trigger assembly 1012 movable connected to the handle housing 1010. The trigger assembly is operable by a surgeon to move the jaw assembly 200 of the end effector 110 from the open state to the closed state as discussed above. The handle 1002 also includes one or more activation triggers 1014 to, for example, initiate the firing of the end effector 110 when in the closed state. A replaceable and/or rechargeable battery pack 1016 is coupled to an end of the handle housing 1010 and provide power to the electrical components located within the handle housing 1010.

Figure 11:
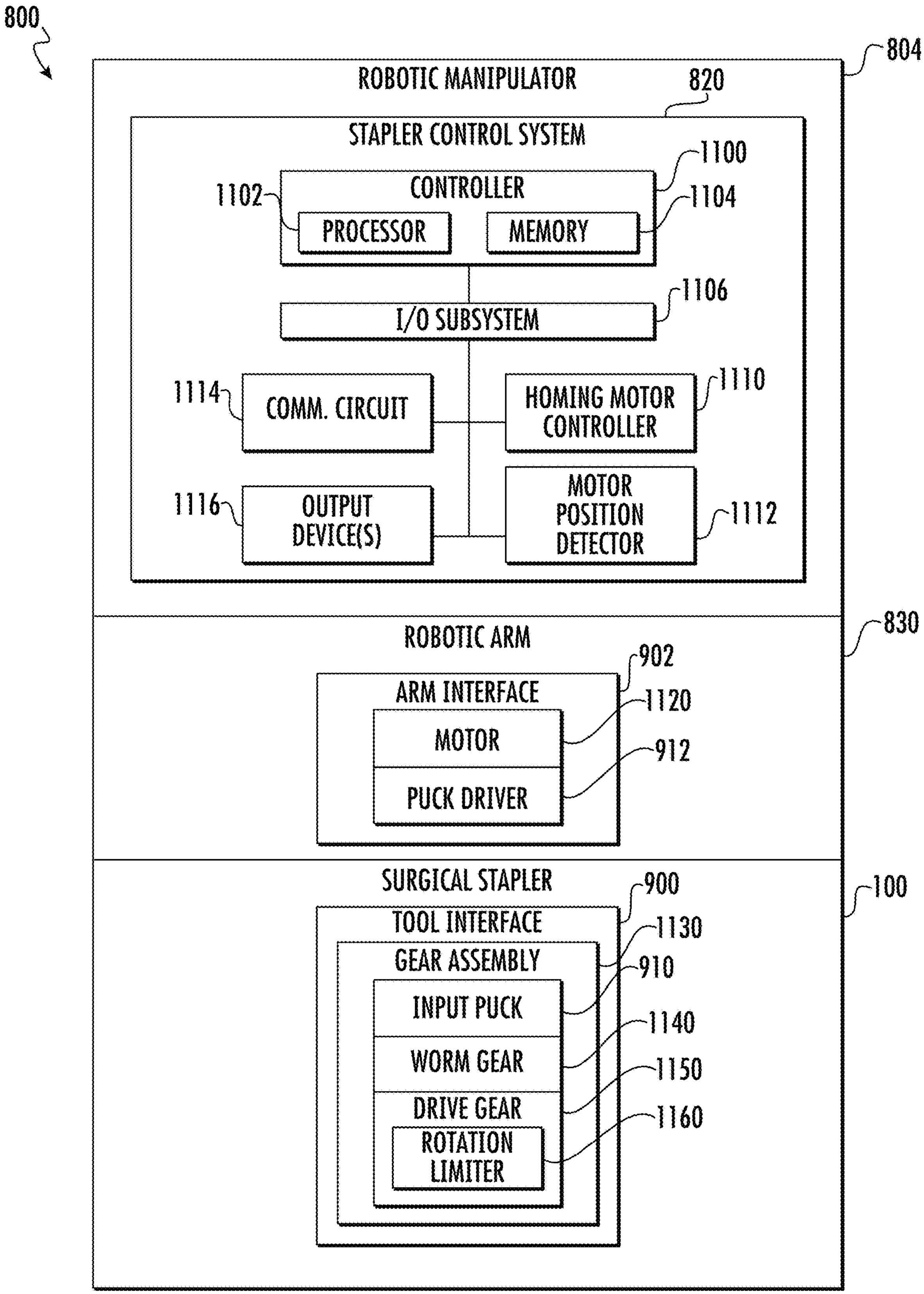
FIG. 11 is a simplified block diagram of another embodiment of a surgical system, similar to the robotic surgical system of FIG. 8, and which includes a motor located in a robotic arm configured to drive a gear assembly of a surgical stapler to control movement of an end effector of the surgical stapler.
Figure 12:
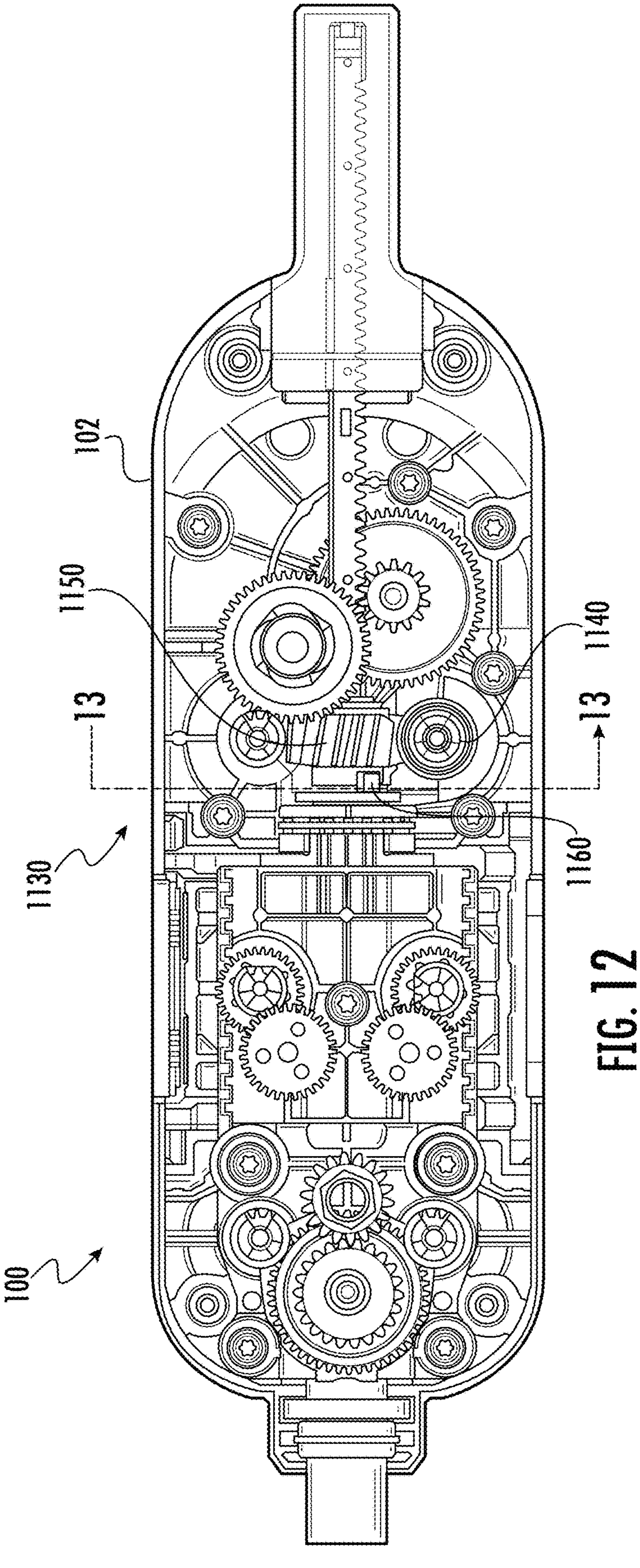
FIG. 12 is a plan view of one embodiment a drive train located in a drive housing of the surgical stapler.

Referring now to FIG. 11, in some embodiments, the control system 820 of the robotic manipulator 804 is configured to determine homing positions of one or more motors 1120 of the robotic surgical system 800 based on parameters of the motors 1120 rather than operational characteristics of the motors 1120, such as operational torque or voltage as discussed in more detail below. The motors 1120 are configured to control movement and operation of the surgical stapler 100 (e.g., movement and/or operation of the end effector 110 of the surgical stapler 100).

As shown in FIG. 11, the robotic arm 830 includes the arm interface 902, which is configured to mate with the tool interface 900 of the surgical stapler 900 as discussed above. The arm interface 902 includes one or more motors 1120, each of is operatively connected to a corresponding one of the puck drivers 912 of the arm interface 902. Similarly, the tool interface 900 includes a gear assembly 1130, which includes one of the input picks 910 configured to mate with the puck driver 912 of the robotic arm 830 to thereby transfer mechanical rotation from the motor 1120 to the surgical stapler 100. The illustrative gear assembly 1130 also includes a worm gear 1140 and a drive gear 1150. The worm gear 1140 is meshed with the drive gear 1150 and operatively coupled to the input puck 910. The gear assembly 1130 may be configured to control operation and/or movement of the end effector 110 such as rotation of the end effector 110.

Figure 13:
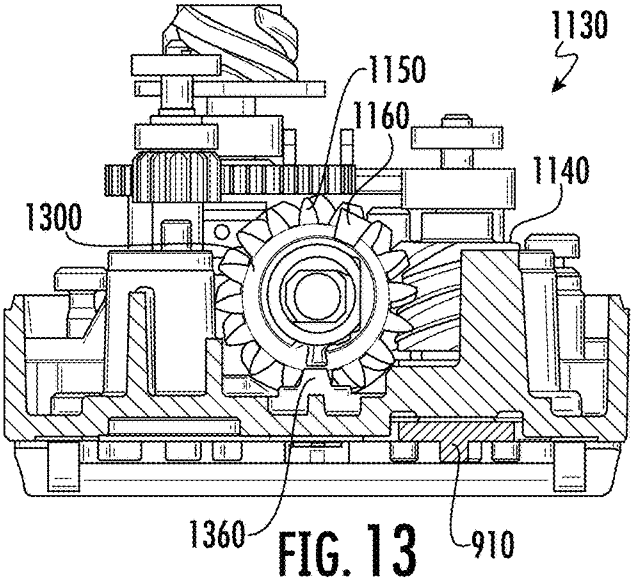
FIG. 13 is a partial cross-sectional view of the drive train of FIG. 12 showing a gear assembly including a drive gear having a rotation limiter configured to contact a rotation hardstop.

In use, as discussed in more detail below, the control system 820 is configured to determine one or more "home" positions for the motor 1120. To do so, the control system 820 determines a target drive voltage for the motor 1120 that is configured to set a speed of the motor 1120 to zero at a reference torque threshold. The reference torque threshold is determined or selected so as to be indicative of contact between the rotation limiter 1160 and a rotation hardstop 1360 (see FIG. 13), which physically limits further rotation of the motor 1120. Illustratively and as discussed in more detail below, the control system 820 is configured to determine the target drive voltage based on pre-defined motor parameters of the motor 1120 (e.g., manufacturer-defined parameters). After the control system 820 has determined the target drive voltage for the motor 1120, the control system 820 may identify or determine the home positions (i.e., the maximum rotational positions of the motor 1120) by controlling the motor 1120 to rotate in a first direction (e.g., a clockwise direction) until the motor stalls, which occurs when the rotation limiter 1160 contacts the rotation hardstop 1360 and the motor torque rises to the reference torque threshold. As discussed below, the control system 820 may be configured to determine stalling of the motor 1120 by monitoring movement of the motor. When the control system 820 determines the motor 1120 has stalled, the control system 820 determines the present position of the motor 1120 (e.g., its rotational position) and sets that determined position as the maximum position (i.e., the "home" position) for the first direction. Subsequently, the control system 820 controls the motor 1120 to rotate in a second direction (e.g., a counter-clockwise direction) until the motor stalls while traveling in the second direction. When the control system 820 determines the motor 1120 has stalled, the control system 820 determines the present position of the motor 1120 (e.g., its rotational position) and sets that determined position as the maximum position (i.e., the "home" position) for the second direction. In this way, the control system 820 may operate the motor 1120 using the determined home positions of the motor 1120 without relying on proxy signals (e.g., torque or voltage) of the motor 1120 during such operation.

The control system 820 may be embodied as any type of controller or control circuit capable of performing the functions described above and further below. Although the control system 820 is illustrated in FIG. 11 and described herein as being included in the robotic manipulator 804, it should be appreciated that, in some embodiments, the control system 820 and the associated functionality may be distributed across multiple components of the robotic surgical system 800, such as the control console 802, the robotic manipulator 804, one or more robotic arms 830, and/or a surgical instrument 840 (e.g., the surgical stapler 100). In such embodiments, the control system 820 may be embodied as a "logical" control system or computer.

In the illustrative embodiment, the control system 820 includes a controller 1100, an I/O subsystem 1106, a homing motor controller 1110, a motor position detector 1112, a communication circuit 1114, and one or more output devices 1116. It should be appreciated, however, that the control system 820 may include other or additional components such as those commonly found in an embedded computer or computer system. Additionally, in some embodiments, one or more of the illustrative components of the control system 820 may be incorporated in, otherwise form a portion of, another component.

The controller 1100 may be embodied as any type of device or collection of devices capable of performing various compute and/or control functions, as described below. In some embodiments, the controller 1100 may be embodied as a single device such as an integrated circuit, an embedded system, a field-programmable-array (FPGA), a system-on-a-chip (SOC), or other integrated system or device. Additionally, in some embodiments, the controller 1100 includes or is embodied as a processor 1102 and memory 1104. The processor 1102 may be embodied as any type of processor capable of performing the functions described herein. For example, the processor 1102 may be embodied as a single or multi-core processor(s), digital signal processor, microcontroller, or other processor or processing/controlling circuit. Similarly, the memory 1104 may be embodied as any type of volatile and/or non-volatile memory and/or data storage capable of storing data generated by or otherwise obtained by the control system 820. In operation, for example, the memory 1104 may store various data and software used during operation of the control system 820 such as operating systems, applications, programs, libraries, and drivers, along with operational data.

The controller 1100 is communicatively coupled to other components of the control system 820 via the I/O subsystem 1106, which may be embodied as circuitry and/or components to facilitate input/output operations with the controller 1100 (e.g., with the processor 1102 and/or memory 1104) and other components of the control system 820. For example, the I/O subsystem 1106 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The homing motor controller 1110 may be embodied as any type of circuit or collection of electronic devices capable of controlling operation of the motor 1120. Similarly, the motor position detector 1112 may be embodied as any electronic device or circuitry capable of determining a present position of the motor 1120. For example, the motor position detector 1112 may be embodied as a motor rotary encoder.

The communication circuit 1114 of the control system 820 may be embodied as any type of communication circuit, device, or collection thereof, capable of enabling communications between the robotic manipulator 804 and the control console 802 over the network 806. To do so, the communication circuit 1114 may utilize any suitable communication protocol including, but not limited to, Ethernet, Wi-Fi (e.g., communications based on the Institute of Electrical and Electronics Engineers (IEEE) 802.11 family), a proprietary protocol, and/or other communication protocols.

The control system 820 also includes one or more output device(s) 1116. Each output device 1116 may be embodied as any type of device or collection of devices capable of generating an output detectable by an operator of the robotic surgical system 800 (e.g., the surgeon 850 operating the control console 802). For example, in some embodiments, the output device(s) 1116 is embodied as, or otherwise includes, a visual output device capable of generating a visual output, such as a display screen (e.g., display 812 of the control system 810 of the control console 802), a light (e.g., a light located on the control console 802 and/or the robotic manipulator 804), and/or other visually-detectable output.

Additionally or alternatively, the output device(s) 1116 is embodied as, or otherwise includes, an audible output device capable of generating an audible output, such as speaker or horn (e.g., a speaker located on the control console 802 and/or on the robotic manipulator 804). Further, in some embodiments, the output device(s) 1116 is embodied as, or otherwise includes, a haptic or tactile output device capable of generating a "touch" output. For example, the output devices 1116 may include a haptic output device incorporated in the input controls 814 of the control console 802 to provide an amount of force-feedback to the surgeon 850. As such, it should be appreciated that the output devices 1116 may include output devices located on the control console 802, the robotic manipulator 804, one or more robotic arms 830, and/or the surgical instrument 840.

As discussed above, the robotic arm 830 includes the arm interface 902, which includes the motor 1120 and the associated puck driver 912. Although only a single motor 1120 and corresponding puck driver 912 are shown in FIG. 11, it should be appreciated that the robotic arm 830 may include additional motors 1120 and associated puck drivers 912 in other embodiments. As described above, the motor 1120 is configured to control movement and/or operation of the end effector 110. In the illustrative embodiment, for example, the motor 1120 controls rotation of the end effector 110.

Additionally, as discussed above, the surgical stapler 100 includes the tool interface 900, which is configured to mate with the arm interface 902 of the robotic arm 900. The tool interface 900 includes the gear assembly 1130, which includes the input puck 910, the worm gear 1140, and the drive gear 1150. Again, although only a single input puck 910, worm gear 1140, and associated drive gear 1150 are shown in FIG. 11, it should be appreciated that the gear assembly 1130 may include additional input pucks 910, worm gears 1140, and drive gears 1150 in other embodiment.

is configured to mate with the tool interface 900 of the surgical stapler 900 as discussed above. The arm interface 902 includes one or more motors 1120, each of is operatively connected to a corresponding one of the puck drivers 912 of the arm interface 902. Similarly, the tool interface 900 includes a gear assembly 1130, which includes one of the input picks 910 configured to mate with the puck driver 912 of the robotic arm 830 to thereby transfer mechanical rotation from the motor 1120 to the surgical stapler 100. The illustrative gear assembly 1130 also includes a worm gear 1140 and a drive gear 1150. The worm gear 1140 is meshed with the drive gear 1150 and operatively coupled to the input puck 910. The gear assembly 1130 may be configured to control operation and/or movement of the end effector 110 such as rotation of the end effector 110.

Figure 14:
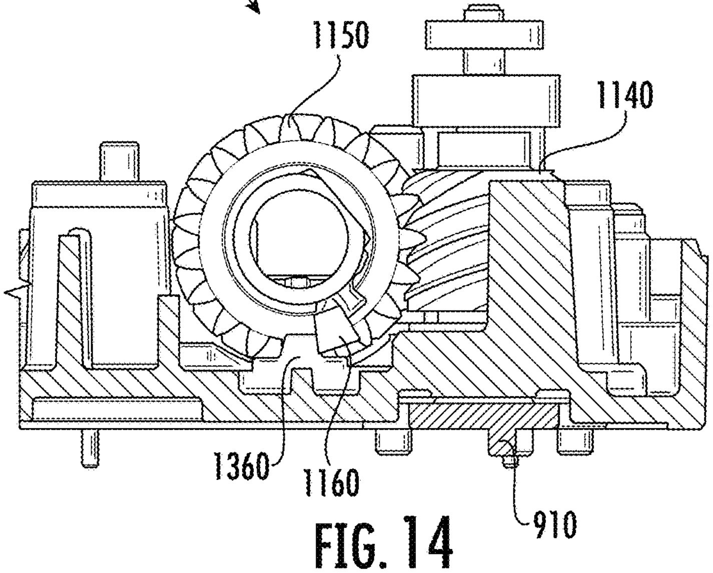
FIG. 14 is another view of the gear assembly of FIG. 13 having the drive gear rotated in a first direction to a maximum position at which the rotation limiter of the drive gear is in contact with the rotation hardstop.
Figure 15:
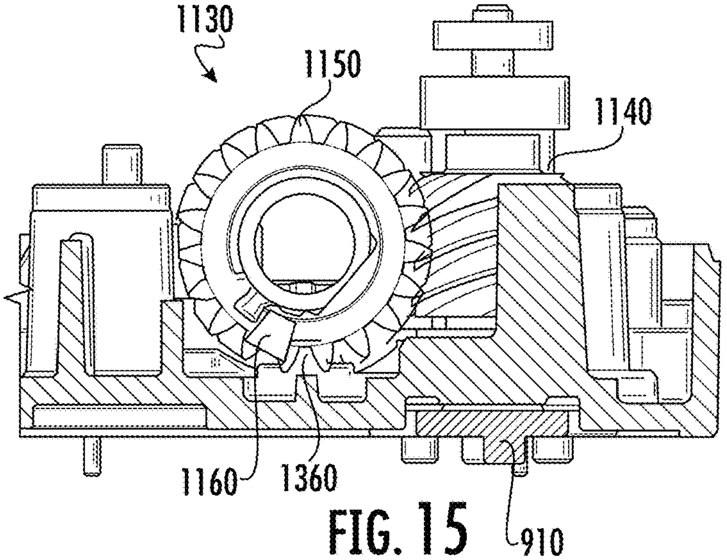
FIG. 15 is another view of the gear assembly of FIG. 13 having the drive gear rotated in a second direction, opposite the first direction, to a maximum position at which the rotation limiter of the drive gear is in contact with the rotation hardstop.

An illustrative gear assembly 1130 located in an associated tool interface 900 is shown in FIGS. 12-15. As discussed above, the input puck 910 is operatively coupled to the worm gear 1140, which is meshed with the drive gear 1150. As shown best in FIG. 13, the drive gear 1150 includes the rotation limiter 1160. Illustratively the rotation limiter 1160 is formed from an extension of a body 1300 of the drive gear 1150. As the drive gear 1150 is rotated via operation of the puck driver 912 and the input puck 910, the rotation limiter 1160 rotates in conjunction with the drive gear 1150. As discussed above, the control system 820 is configured to determine home positions for the motor 1120 by rotating the motor 1120 in a first direction (as shown in FIG. 14) and rotation the motor 1120 in a second direction (as shown in FIG. 15) until the motor 1120 stalls. As discussed above, contact between the rotation limiter 1160 and the rotation hardstop 1360 will stall the motor 1120 once the present torque of the motor surpasses the reference torque threshold because the target drive voltage of the motor 1120 has been selected such that the speed of the motor is zero at the reference torque threshold. Again, as discussed above, the control system 820 sets the position of the motor 1120 at the time of stall to the maximum (i.e., "home") positions for either direction.

Referring now to FIG. 16, in use, the control system 820 may execute a method 1600 for homing the motor 1120. The method 1600 begins with block 1602 in which the control system 820 determines whether to perform an initialization of the surgical stapler 100, which may include the determination of the homing positions of the motor 1120. If so, the method 1600 advances to block 1604.

In block 1604, the control system 820 determines a target drive voltage for the motor 1120 that is required to set the speed of the motor 1120 to zero at a reference torque threshold. To do so, in some embodiments, the control system 820 may retrieve the target drive voltage form a data storage (e.g., when the targe drive voltage is determined prior to initialization) in block 1606. Alternatively, in other embodiments, the control system 820 may determine the targe drive volage based on motor parameters of the motor 1120 in block 1608. The motor parameters may be embodied as relatively constant parameters defined by, for example, the manufacturer of the motor 1120. In some embodiments, the control system 820 may determine or estimate the motor parameters by performing a calibration procedure in block 1610. The calibration procedure may include, for example, movement of the motor 1120 and monitoring of operational characteristics of the motor during such movement.

Figure 17:
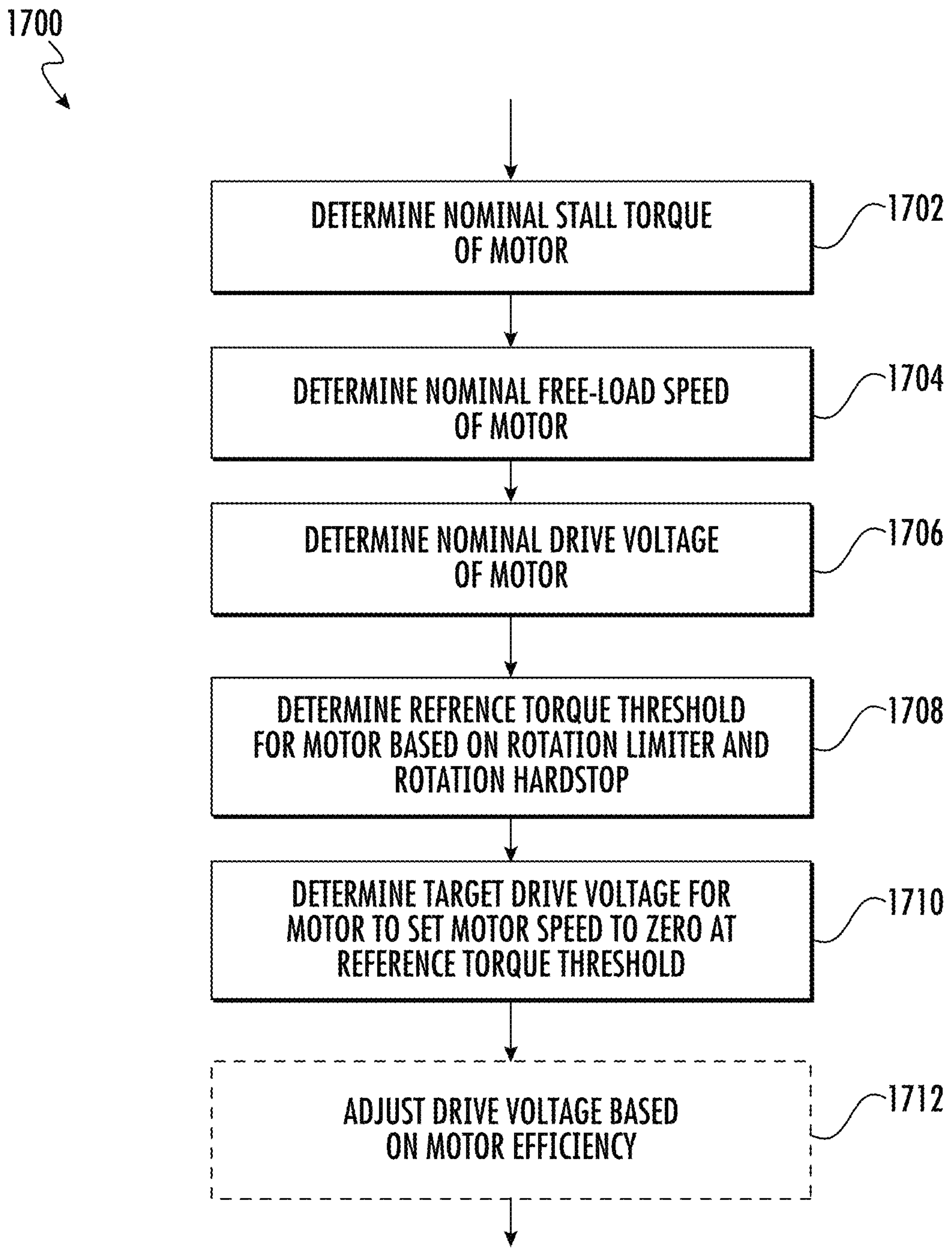
FIG. 17 is a simplified flow diagram of a method for determining a target drive voltage for a motor to set a speed of the motor to zero at a reference torque threshold.

In some embodiments, as shown in FIG. 17, the control system 820 may be configured to execute a method 1700 for determine the target drive voltage of the motor 1120 based on motor parameters of the motor 1120. The method 1700 begins with block 1702 in which the control system 820 determines a nominal stall torque ($T_{stall}$) of the motor 1120. In block 1704, the control system 820 determines a nominal free-load speed ($S_{free}$) of the motor 1120. Additionally, in block 1706, the control system 820 determines a nominal drive voltage ($V_{nom}$) of the motor 1120. Again, as discussed above, each of the nominal stall torque value, the nominal free-load speed value, and the nominal drive voltage value may be predefined values provided by the manufacturer of the motor 1120 and retrievable therefrom.

In block 1708, the control system 820 determines a reference torque threshold for the motor 1120. Illustratively, the reference torque threshold is based on the physical properties of the rotation limiter 1160 and the rotation hardstop 1360. That is, the reference torque threshold is determined such that the reference torque is indicative of contact between the rotation limiter 1160 and the rotation hardstop 1360 without causing damage to either component or the motor 1120 (e.g., overheating of the motor 1120). For example, in the illustrative embodiment, the reference torque threshold is set to 0.1 Newton-meters (nm).

Subsequently, in block 1710, the control system 820 is configured to determine a target drive voltage for the motor 1120 that sets the speed of the motor 1120 to zero at the reference torque threshold determined in block 1708. To do so, the control system 820 determines the target drive voltage based on the nominal stall torque value determined in block 1702, the nominal free-load speed value determined in block 1704, the nominal drive voltage value determined in block 1706, and the reference torque threshold determined in block 1708. For example, in the illustrative embodiment, the control system 820 is configured to determine the target drive voltage according to the following equation:

$$S_{motor}=((V_{target}/V_{nom})*S_{free})-(S_{free}/T_{stall})*T_{ref},$$

wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

Figure 18:
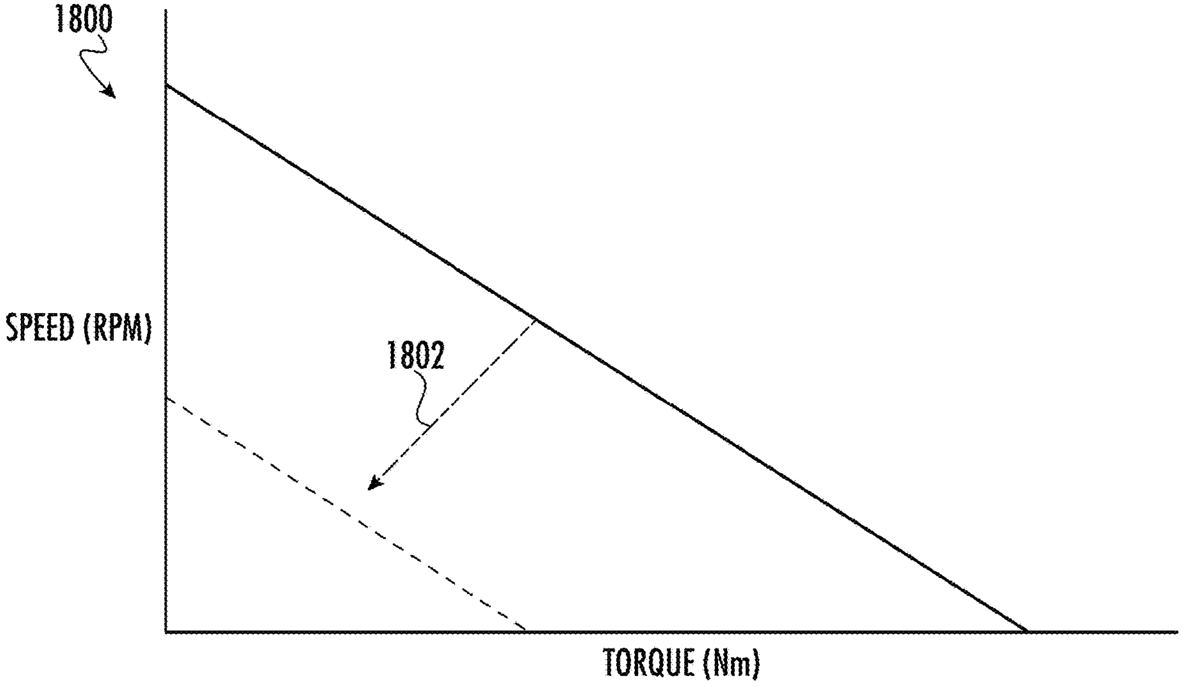
FIG. 18 is a simplified graph illustrating motor speed to motor torque.

It should be appreciated that the speed of the motor, $S_{motor}$, and the resulting torque of the motor 1120 have a constant relationship, regardless of the other motor parameters as illustrated in the graph 1800 of FIG. 18. As such, while different motor parameters may shift the relationship trendline, as indicated by arrow 1802, the slope of the trendline remains relatively constant.

Referring back to FIG. 17, after the control system 820 has determined the targe drive voltage in block 1710, the method 1700 advances to block 1712 in some embodiments. In block 1712, the control system 820 may adjust the target drive voltage based on an efficiency of the motor 1120. For example, if the motor 1120 is indicated as being 95% efficient, the determined target drive voltage (or voltage threshold) may be increased by 5%.

Referring now back to FIG. 16, after the control system 812 has determined the target drive voltage for motor 1120 in block 1604, the method 1600 advances to block 1612. In block 1612, the control system 812 controls the motor 1120 to move in a first direction (e.g., clockwise) using the target drive voltage until the motor stalls. As discussed above, the target drive voltage is determined such that the motor 1120 stalls when the motor torque exceeds the reference torque threshold, which is indicative of contact between the rotation limiter 1160 and the rotation hardstop 1360. In block 1614, the control system 820 may determine or verify that the motor 1120 has stalled by monitoring movement of the motor 1120 as sensed by the motor position detector 1112.

Subsequently, in block 1616, the control system 820 sets the present position of the motor 1120 as the maximum position (e.g., the "home" position) for the first direction. Additionally, in block 1618, the control system 812 controls the motor 1120 to move in a second direction (e.g., counterclockwise), opposite the first direction, using the target drive voltage until the motor stalls again. In block 1620, the control system 820 sets the present position of the motor 1120 as the maximum position (e.g., the "home" position) for the second direction. After the control system 820 has determined the home positions for the motor 1120, the control system 820 may operation the surgical stapler 100 using the determined home or maximum motor positions in block 1622.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

EXAMPLES

Example 1 includes a robotic surgical system having a robotic surgical stapler, a robotic arm, and a control system. The robotic surgical stapler includes a drive housing, an elongated shaft extending from the drive housing, an end effector located at a distal end of the elongated shaft, and a gear assembly located in the drive housing and configured to control movement of the end effector. The gear assembly includes a drive gear having a rotation limiter configured to contact a rotation hardstop to limit rotation of the diver gear. The robotic arm includes a motor operably coupled to the gear assembly of the robotic surgical stapler and configured to rotate the drive gear to control movement of the end effector. The control system is configured to control operation of the motor to control movement of the end effector. The control system is further configured to determine a target drive voltage for the motor, wherein the target drive voltage is configured to set a speed of the motor to zero at a reference torque threshold, control the motor to rotate in a first direction using the target drive voltage until the motor stalls, wherein the stalling of the motor is indicative of contact between the rotation limiter of the gear assembly and the rotation hardstop, determine, in response to the stalling of the motor in response to rotation in the first direction, a first position of the motor, and set the first position of the motor as a maximum motor position for the first direction.

Example 2 includes the subject matter of Example 1, and wherein to control the motor to rotate in the first direction using the target drive voltage until the motor stalls includes monitoring movement of the motor while rotating the motor in the first direction, and determining that the motor has stalled in response to detecting that the motor has stopped moving.

Example 3 includes the subject matter of any of Examples 1 or 2, and wherein the control system is further configured to control the motor to rotate in a second direction, opposite the first direction, using the target drive voltage until the motor stalls; determine, in response to the stalling of the motor in response to rotation in the second direction, a second position of the motor; and set the second position of the motor as a maximum motor position for the second direction.

Example 4 includes the subject matter of any of Examples 1-3, and wherein to determine the target drive voltage includes to retrieve the target drive voltage from a data storage.

Example 5 includes the subject matter of any of Examples 1-4, and wherein to determine the target drive voltage includes to determine the target drive voltage based on motor parameters of the motor.

Example 6 includes the subject matter of any of Examples 1-5, and wherein the control system is further configured to perform a calibration process to estimate the motor parameters of the motor.

Example 7 includes the subject matter of any of Examples 1-6, and wherein to determine the target drive voltage includes to determine a nominal stall torque of the motor; determine a nominal free-load speed of the motor; determine a nominal drive voltage of the motor; determine the reference torque threshold for the motor based on a physical property of the rotation limiter and the rotation hardstop; and determine the target drive voltage that sets the speed of the motor to zero at the reference torque threshold based on the nominal stall torque, the nominal free-load speed, and the nominal drive voltage of the motor.

Example 8 includes the subject matter of any of Examples 1-7, and wherein to determine the target drive voltage comprises to determine the target drive voltage according to the following equation: $S_{motor}=((V_{target}/V_{nom})*S_{free})-(S_{free}/T\ stall)*T_{ref}$, wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

Example 9 includes the subject matter of any of Examples 1-8, and wherein the control system is further configured to determine an efficiency of the motor and adjust the target drive voltage based on the efficiency.

Example 10 includes the subject matter of any of Examples 1-9, and wherein the robotic arm includes an arm interface having a puck driver controlled by the motor. The gear assembly of the surgical stapler further includes an input puck configured to mate with the puck driver to transfer rotational movement from the puck driver to the drive gear.

Example 11 includes the subject matter of any of Examples 1-10, and wherein the gear assembly further includes a worm gear operatively coupled to the input puck and meshed with the drive gear.

Example 12 includes the subject matter of any of Examples 1-11, and wherein the control system is further configured to control operation of the surgical stapler to perform a surgical procedure using the maximum motor position for the first direction and the second direction.

Example 13 includes a method for homing a motor of a surgical stapler system. The method includes determining, by a control system, a target drive voltage for the motor, wherein the target drive voltage is configured to set a speed of the motor to zero at a reference torque threshold; controlling, by the control system, the motor to rotate in a first direction using the target drive voltage; monitoring, by the control system, movement of the motor while the motor is rotated in the first direction; determining, by the control system, that the motor has stalled in response to a determination that the motor has stopped moving; determining, by the control system and in response to the stalling of the motor, a first position of the motor, and setting, by the control system, the first position of the motor as a maximum motor position for the first direction.

Example 14 includes the subject matter of Example 13, and further including controlling, by the control system, the motor to rotate in a second direction, opposite the first direction, using the target drive voltage until the motor stalls; determining, by the control system and in response to the stalling of the motor in response to rotation in the second direction, a second position of the motor; and setting, by the control system, the second position of the motor as a maximum motor position for the second direction.

Example 15 includes the subject matter of any of Examples 13 or 14, and wherein determining the target drive voltage includes determining the target drive voltage based on motor parameters of the motor.

Example 16 includes the subject matter of any of Examples 1-15, and further including performing, by the control system, a calibration process to estimate the motor parameters of the motor.

Example 17 includes the subject matter of any of Examples 1-16, and wherein determining the target drive voltage includes determining, by the control system, a nominal stall torque of the motor; determining, by the control system, a nominal free-load speed of the motor; determining, by the control system, a nominal drive voltage of the motor; determining, by the control system, the reference torque threshold for the motor based on a physical property of the rotation limiter and the rotation hardstop; and determining, by the control system, the target drive voltage that sets the speed of the motor to zero at the reference torque threshold based on the nominal stall torque, the nominal free-load speed, and the nominal drive voltage of the motor.

Example 18 includes the subject matter of any of Examples 1-17, and wherein determining the target drive voltage includes determining the target drive voltage according to the following $S_{motor}=((V_{target}/V_{nom})*S_{free})-(S_{free}/T_{stall})*T_{ref}$, wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

Example 19 includes the subject matter of any of Examples 1-18, and further including determining, by the control system, an efficiency of the motor and adjust the target drive voltage based on the efficiency.

Example 20 includes the subject matter of any of Examples 1-19, and further including controlling, by the control system, operation of the surgical stapler to perform a surgical procedure using the maximum motor position for the first direction and the second direction.

The invention claimed is:

1. A robotic surgical system comprising:

a robotic surgical stapler comprising a drive housing, an elongated shaft extending from the drive housing, an end effector located at a distal end of the elongated shaft, and a gear assembly located in the drive housing and configured to control movement of the end effector, wherein the gear assembly includes a drive gear having a rotation limiter configured to contact a rotation hardstop to limit rotation of the diver gear;

a robotic arm comprising a motor operably coupled to the gear assembly of the robotic surgical stapler and configured to rotate the drive gear to control movement of the end effector; and a control system configured to control operation of the motor to control movement of the end effector, wherein the control system is further configured to:

determine a target drive voltage for the motor, wherein the target drive voltage is configured to set a speed of the motor to zero at a reference torque threshold, control the motor to rotate in a first direction using the target drive voltage until the motor stalls, wherein the stalling of the motor is indicative of contact between the rotation limiter of the gear assembly and the rotation hardstop, determine, in response to the stalling of the motor in response to rotation in the first direction, a first position of the motor, and set the first position of the motor as a maximum motor position for the first direction.

2. The robotic surgical system of claim 1, wherein to control the motor to rotate in the first direction using the target drive voltage until the motor stalls comprises:

monitoring movement of the motor while rotating the motor in the first direction; and determining that the motor has stalled in response to detecting that the motor has stopped moving.

3. The robotic surgical system of claim 1, wherein the control system is further configured to:

control the motor to rotate in a second direction, opposite the first direction, using the target drive voltage until the motor stalls;

determine, in response to the stalling of the motor in response to rotation in the second direction, a second position of the motor; and set the second position of the motor as a maximum motor position for the second direction.

4. The robotic surgical system of claim 1, wherein to determine the target drive voltage comprises to retrieve the target drive voltage from a data storage.

5. The robotic surgical system of claim 1, wherein to determine the target drive voltage comprises to determine the target drive voltage based on motor parameters of the motor.

6. The robotic surgical system of claim 5, wherein the control system is further configured to perform a calibration process to estimate the motor parameters of the motor.

7. The robotic surgical system of claim 5, wherein to determine the target drive voltage comprises to:

determine a nominal stall torque of the motor;

determine a nominal free-load speed of the motor;

determine a nominal drive voltage of the motor;

determine the reference torque threshold for the motor based on a physical property of the rotation limiter and the rotation hardstop; and determine the target drive voltage that sets the speed of the motor to zero at the reference torque threshold based on the nominal stall torque, the nominal free-load speed, and the nominal drive voltage of the motor.

8. The robotic surgical system of claim 5, wherein to determine the target drive voltage comprises to determine the target drive voltage according to the following equation:

$$S_{motor} = ((V_{target} / V_{nom}) * S_{free}) - (S_{free} / T_{stall}) * T_{ref}$$

wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

9. The robotic surgical system of claim 5, wherein the control system is further configured to determine an efficiency of the motor and adjust the target drive voltage based on the efficiency.

10. The robotic surgical system of claim 1, wherein the robotic arm includes an arm interface having a puck driver controlled by the motor, and wherein the gear assembly of the surgical stapler further includes an input puck configured to mate with the puck driver to transfer rotational movement from the puck driver to the drive gear.

11. The robotic surgical system of claim 10, wherein the gear assembly further includes a worm gear operatively coupled to the input puck and meshed with the drive gear.

12. The robotic surgical system of claim 1, wherein the control system is further configured to control operation of the surgical stapler to perform a surgical procedure using the maximum motor position for the first direction and the second direction.

13. A method for homing a motor of a surgical stapler system, the method comprising:

determining, by a control system, a target drive voltage for the motor, wherein the target drive voltage is configured to set a speed of the motor to zero at a reference torque threshold;

controlling, by the control system, the motor to rotate in a first direction using the target drive voltage;

monitoring, by the control system, movement of the motor while the motor is rotated in the first direction;

determining, by the control system, that the motor has stalled in response to a determination that the motor has stopped moving;

determining, by the control system and in response to the stalling of the motor, a first position of the motor, and setting, by the control system, the first position of the motor as a maximum motor position for the first direction.

14. The method of claim 13, further comprising:

controlling, by the control system, the motor to rotate in a second direction, opposite the first direction, using the target drive voltage until the motor stalls;

determining, by the control system and in response to the stalling of the motor in response to rotation in the second direction, a second position of the motor; and setting, by the control system, the second position of the motor as a maximum motor position for the second direction.

15. The method of claim 13, wherein determining the target drive voltage comprises determining the target drive voltage based on motor parameters of the motor.

16. The method of claim 15, further comprising performing, by the control system, a calibration process to estimate the motor parameters of the motor.

17. The method of claim 15, wherein determining the target drive voltage comprises:

determining, by the control system, a nominal stall torque of the motor;

determining, by the control system, a nominal free-load speed of the motor;

determining, by the control system, a nominal drive voltage of the motor;

determining, by the control system, the reference torque threshold for the motor based on a physical property of the rotation limiter and the rotation hardstop; and determining, by the control system, the target drive voltage that sets the speed of the motor to zero at the reference torque threshold based on the nominal stall torque, the nominal free-load speed, and the nominal drive voltage of the motor.

18. The method of claim 15, wherein determining the target drive voltage comprises determining the target drive voltage according to the following equation:

$$S_{motor} = ((V_{target} / V_{nom}) * S_{free}) - (S_{free} / T_{stall}) * T_{ref}$$

wherein $S_{motor}$ is the speed of the motor set to zero, $V_{target}$ is the target drive voltage of the motor, $V_{nom}$ is the nominal drive voltage of the motor, $S_{free}$ is the nominal free-load speed of the motor, $T_{stall}$ is the nominal stall torque of the motor, and $T_{ref}$ is the reference torque threshold.

19. The method of claim 15, further comprising determining, by the control system, an efficiency of the motor and adjust the target drive voltage based on the efficiency.

20. The method of claim 13, further comprising controlling, by the control system, operation of the surgical stapler to perform a surgical procedure using the maximum motor position for the first direction and the second direction.

* * * * *